US012709754B2

(12) United States Patent
Zhu et al.

(10) Patent No.: US 12,709,754 B2
(45) Date of Patent: Aug. 18, 2026

(54) REGULATION OF VON WILLEBRAND FACTOR (VWF)

(71) Applicant: BAND THERAPEUTICS, LLC, Belmont, MA (US)

(72) Inventors: Shuhao Zhu, Concord, MA (US); James C. Gilbert, Bethlehem, CT (US)

(73) Assignee: Band Therapeutics, LLC, Belmont, MA (US)

( * ) Notice: Subject to any disclaimer, the term of this patent is extended or adjusted under 35 U.S.C. 154(b) by 894 days.

(21) Appl. No.: 17/797,309

(22) PCT Filed: Feb. 3, 2021

(86) PCT No.: PCT/US2021/016290
§ 371 (c)(1),
(2) Date: Aug. 3, 2022

(87) PCT Pub. No.: WO2021/158583
PCT Pub. Date: Aug. 12, 2021

(65) Prior Publication Data

US 2023/0038761 A1 Feb. 9, 2023

Related U.S. Application Data

(60) Provisional application No. 62/969,762, filed on Feb. 4, 2020.

(51) Int. Cl.
*C12N 15/115* (2010.01)
*A61P 7/02* (2006.01)

(52) U.S. Cl.
CPC .............. *C12N 15/115* (2013.01); *A61P 7/02* (2018.01); *C12N 2310/113* (2013.01); *C12N 2310/16* (2013.01)

(58) Field of Classification Search
None
See application file for complete search history.

(56) References Cited

U.S. PATENT DOCUMENTS

| | | | | |
|---|---|---|---|---|
| 11,060,094 | B2 * | 7/2021 | Zhu | C07H 21/02 |
| 2009/0149643 | A1 | 6/2009 | Diener et al. | |
| 2009/0203766 | A1 | 8/2009 | Gilbert et al. | |
| 2012/0264815 | A1 | 10/2012 | Sullenger et al. | |
| 2016/0289297 | A1 | 10/2016 | Sullenger et al. | |
| 2018/0305695 | A1 | 10/2018 | Hirao et al. | |
| 2024/0002861 | A1 * | 1/2024 | Gilbert | A61P 7/00 |
| 2024/0417739 | A1 * | 12/2024 | Gilbert | A61K 31/712 |

FOREIGN PATENT DOCUMENTS

| | | | |
|---|---|---|---|
| WO | WO 2010/091396 | A2 | 8/2010 |
| WO | 2018053427 | A1 | 3/2018 |
| WO | WO 2018/213697 | A1 | 11/2018 |

OTHER PUBLICATIONS

International Search Report for PCT/US2021/016290 dated Apr. 28, 2021 (4 pages).

* cited by examiner

*Primary Examiner* — Brian Whiteman
(74) *Attorney, Agent, or Firm* — Proskauer Rose LLP

(57) ABSTRACT

The present disclosure relates to agents, compositions targeting to von Willebrand factor (VWF). The VWF targeting agents are synthetic polynucleotides, including VWF binding agents and their reversal agents. The VWF binding agents are VWF binding aptamers that bind to and inhibit the VWF activities. The VWF binding agents can be reversed using reversal agents to reverse the inhibitory effect and thereby restore VWF activities. The disclosure further provides methods for regulating the activities of VWF, thereby modulating VWF mediated platelet functionality, such as thrombosis, the present VWF targeting agents may be used for preventing thrombus formation and treating thrombotic disorders.

15 Claims, 10 Drawing Sheets

Specification includes a Sequence Listing.

FIG. 2

REGULATION OF VON WILLEBRAND FACTOR (VWF)

REFERENCE TO RELATED APPLICATIONS

The present application is a 35 U.S.C. § 371 National Stage Application of International Application No. PCT/US2021/016290, filed Feb. 3, 2021, which claims priority to U.S. Provisional Application No. 62/969,762, filed on Feb. 4, 2020; the contents of which are incorporated herein by reference in their entirety.

REFERENCE TO THE SEQUENCE LISTING

The present application is being filed along with a Sequence Listing in electronic format. The Sequence Listing is provided as a file entitled GBT-005US1-ST25.txt, created on Aug. 2, 2022, which is 40,657 bytes in size. The information in the electronic format of the sequence listing is incorporated herein by reference in its entirety.

FIELD OF THE DISCLOSURE

The present disclosure relates to agents, compositions and methods for regulating the activity of von Willebrand factor (VWF), thereby modulating VWF mediated platelet activities, such as thrombosis.

BACKGROUND OF THE DISCLOSURE von Willebrand factor (VWF) is a large, multimeric glycoprotein (~0.5-10 Mda) and plays a key role in normal hemostasis and thrombosis which demonstrates a dual role between these two processes. VWF is primarily expressed and stored in endothelial cells and platelets. Secreted extracellular VWF is a key bridge factor that links subendothelial collagen (e.g., exposed collagen from the injured vessel wall) to platelets in the circulation, thereby initiating platelet adhesion and aggregation to the damage sites of vascular vessel wall upon vessel injury. VWF mediated initiation of platelet adhesion to the vascular wall is the fundamental and central step in thrombus formation, which is physiological response to a damage that undermines vascular wall integrity.

The levels of plasma VWF are important for hemostatic balance. Decreasing or increasing the VWF levels in the blood can tip the balance and cause many diseases. Deficiencies in VWF (e.g., quantitative or qualitative defects in VWF) lead to von Willebrand disease (VWD), the most common inherited bleeding disorder. Abnormal VWF concentrations or function can also cause severe medical disorders like venous thromboembolic disease (VTE).

There is accumulated evidence indicating a positive correlation between excessive levels of plasma VWF and major thrombotic disorders. Elevated levels of plasma VWF are not only independent risk factors for coronary heart disease and stroke, but also positively associated with severity and poor clinical outcome of thromboembolic cardiovascular events. It has been reported that atherosclerosis and related thrombotic occlusions are correlated with increased levels of VWF (Reviewed by Shahidi, Thrombosis and von Willebrand Factor; *Adv Exp Biol.* 2017; 906:285-306). The association of high levels of VWF and stroke, including the association of VWF levels with the risk of first-ever ischemic stroke, stroke recurrence, stroke severity and post-stroke morbidity and mortality, has been recently reported by, e.g., Licata et al., Immuno-inflammatory activation in acute cardio-embolic strokes in comparison with other subtypes of ischaemic stroke. *Thromb Haemost.* 2009; 101:929-937; Bongers et al., Lower levels of ADAMTS13 are associated with cardiovascular disease in young patients. *Atherosclerosis,* 2009; 207:250-254; Catto et al., Willebrand factor and factor VIII: C in acute cerebrovascular disease. Relationship to stroke subtype and mortality. *Thromb Haemost.* 1997; 77:1104-1108; Qizilbash et al., Von Willebrand factor and risk of ischemic stroke. *Neurology.* 1997; 49:1552-1556; Bongers et al, High von Willebrand factor levels increase the risk of first ischemic stroke: influence of ADAMTS13, inflammation, and genetic variability. *Stroke.* 2006; 37:2672-2677; Williams et al., Genetic drivers of von Willebrand factor levels in an ischemic stroke population and association with risk for recurrent stroke. *Stroke;* 2017; 48 (06): 1444-1450; and reviewed by Denorme and De Meyer, the VWF-GPIb axis in ischemic stroke: lessons from animal models. *Thromb Haemost.* 2016; 116 (04): 597-604.

Recent studies have shown that elevated levels of VWF contribute to various other pathological conditions as well, such as inflammation (Starke et al., Endothelial von Willebrand factor regulates angiogenesis. *Blood;* 2011; 117:1071-1080), angiogenesis ((Lenting et al., von Willebrand factor: the old, the new and the unknown. *J Thromb Haemost;* 2012; 10:2428-2437) and cancer metastasis (Terraube et al., Role of von Willebrand factor in tumor metastasis, *Thromb Res,* 2007; 120 (Suppl. 2): S64-70).

Given its role in thrombosis and other vascular diseases, VWF has been an emerging target for treatment of thrombotic disorders, e.g., in stroke therapy (Buchtele et al., Targeting von Willebrand Factor in Ischaemic Stroke: Focus on Clinical Evidence; *Thromb Haemost.* 2018; 118 (6): 959-978).

Agents aiming to regulate VWF activities include those can modulate VWF levels and/or can interfere VWF-mediated platelet adhesion and thrombus formation. Several promising preclinical and clinical studies have demonstrated that the antithrombotic potential of agents that inhibits VWF function could be useful in stroke therapy and prevention (De Meyer et al., von Willebrand factor: an emerging target in stroke therapy, *Stroke.* 2012; 43 (2): 599-606). Such agents include for example, monoclonal antibodies (De Meyer et al., Development of monoclonal antibodies that inhibit platelet adhesion or aggregation as potential anti-thrombotic drugs. *Cardiovasc Hematol Disord Drug Targets.* 2006; 6:191-207), aptamers (Diener et al., Inhibition of von Willebrand factor-mediated platelet activation and thrombosis by the anti-von Willebrand factor A1-domain aptamer ARC1779. *J Thromb Haemost.* 2009; 7:1155-1162) and recombinant inhibitory fragments (e.g., GPG-290) (Wadanoli et al., The von Willebrand factor antagonist (GPG-290) prevents coronary thrombosis without prolongation of bleeding time. *Thromb Haemost.* 2007; 98:397-405).

The dual roles of VWF in thrombotic and bleeding events indicate the level of VWF needs to be tightly regulated in the context of a specific physiological condition. Complete and long-term inhibition of VWF also deplete its function to recruit platelets to damaged vessels to block bleeding. Similar to other anti-thrombotic drugs, an adverse event associate with use of anti-VWF aptamers is prone to bleeding. Excessive bleeding can in severe cases, can cause permanent disability and even death (Ebbesen et al., Drug-related deaths in a department of internal medicine, *Arch Intem Med.,* 2001; 161 (9): 2317-2323). Though in the case of thrombotic diseases, such as ischemic stroke, a physician may trade off an increased risk of bleeding to use a drug to reduce the ischemic complications in a patient, some bleeding events, e.g., particularly those that require blood transfusion have a significant impact on the outcome in patients. Frequent bleeding is often associated with significant increase in short-term mortality.

In the cases that an aptamer that binds to and inhibits VWF activity is used for blocking the formation of blood clots for treating/preventing stroke, the inhibitory function of such aptamer needs to be reversed to increase the clotting in a condition that needs to reduce the risk of bleeding such as surgery.

The present disclosure provides methods relating to use of anti-VWF aptamers and their antidotes as reversal agents to manipulate VWF levels and activities in various clinical conditions. These VWF agents can be used to prevent thrombus formation and/or treat thrombotic disorders.

BRIEF DESCRIPTION OF THE DRAWINGS

FIG. 2 shows the interaction of BT101 with BT100 (SEQ ID NO.: 5; the core aptamer of BT200) at molar ratios of 0:1, 1:0, 1:2:1:1, 1:0.5, and 1:0.2 evaluated using PAGE. The bands corresponding to BT101, BT100, and the duplex resulting from the binding of the two are indicated by the arrows.

SUMMARY OF THE DISCLOSURE

Figure 1B:
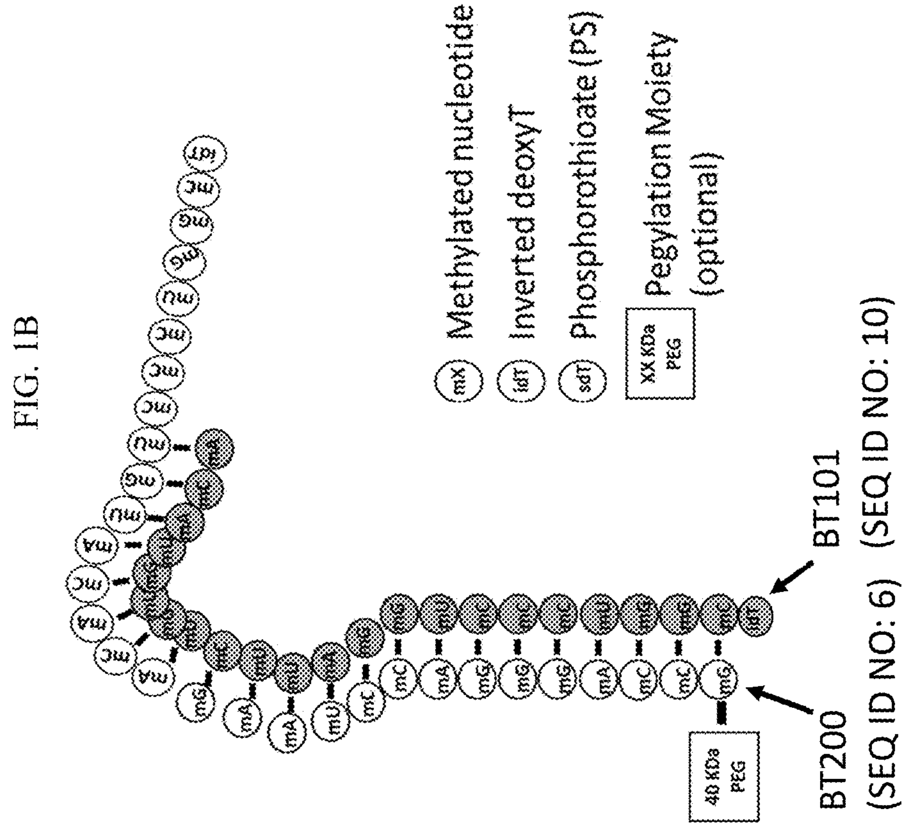
FIG. 1A is structure of BT200 and FIG. 1B depicts the binding of BT200 to its reversal agent, BT101.
Figure 1A:
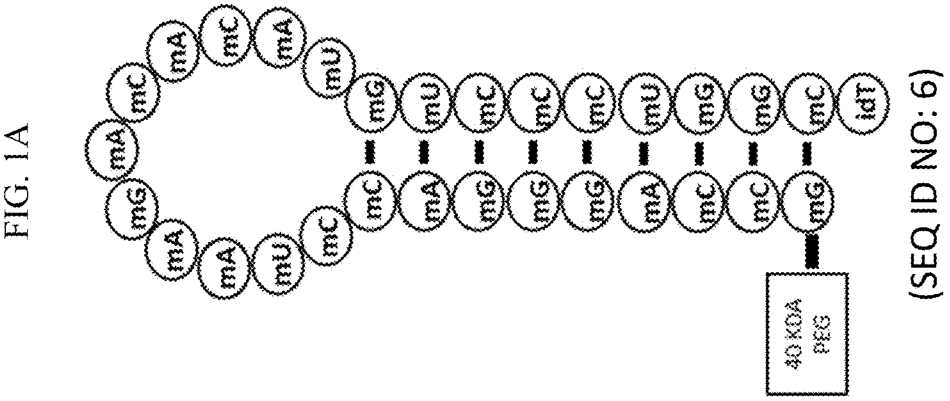

In one aspect, the present disclosure provides methods of treating, preventing, or preventing the progression of, or alleviating thrombosis (i.e., thrombus formation) associated with a clinical condition in a patient in need comprising administrating to the patient an effective amount of a VWF binding agent that comprises a nucleic acid sequence that binds to and inhibits the activity of VWF; and optionally administering to the patient a therapeutically effective amount of a reversal agent that reverses the effect of the VWF binding agent and that comprises a second nucleic acid sequence complementary to the sequence or a portion of the sequence of the VWF binding agent. In accordance, the reversal agent is administered when the patient receiving the treatment of the VWF binding agent and compositions thereof is under the threat of hemorrhage.

In some embodiments, the thrombotic clinical condition is a cardiovascular disease or a cerebrovascular disease that includes ischemic stroke, transient ischemic attack (TIA), silent stroke, primary stroke, secondary stroke, embolic stroke, pulmonary embolism, deep venous thrombosis (DVT), silent new cerebral infarction lesions detected by MRI imaging, acute minor ischemic stroke, stenosed coronary arteries, cerebrovascular thrombi, extracranial large artery atherosclerosis (LAA), intracranial LAA, small artery occlusion, occlusive thrombi, acute coronary syndrome, and acute occlusion thrombosis.

In some embodiments, the thrombus formation is in veins, arteries or cardiac chambers.

In some embodiments, the patient under the threat of hemorrhage is scheduled for a clinical surgery.

In some embodiments, the VWF binding agent is an aptamer comprising a nucleic acid sequence that binds to VWF and the reversal agent is an antidote of the VWF aptamer, which comprising a complementary sequence of the nucleic acid sequence of the VWF binding aptamer.

In some embodiments, the VWF binding agent is a VWF binding aptamer comprises the nucleic acid sequence presented by SEQ ID No.: 3, or variant thereof; and the reversal agent comprises the nucleic acid sequence presented by SEQ ID No.: 9, or variant thereof.

In some embodiments, the VWF binding agent and its reversal agent may include at least one chemical modification.

In some embodiments, the VWF binding agent and its reversal agent include at least one nucleotide modification with 2'-O-methyl modification.

In Some embodiments, the VWF binding agent is further modified with a conjugate selecting from the group consisting of a polymer (e.g., a PEG polymer), a protein, an antibody or variant thereof, a peptide, a lipid, a fatty acid, a carbohydrate, and a small molecule.

In some embodiments, the reversal agent is modified with a conjugate selecting from the group consisting of a PEG polymer, a protein, an antibody or variant thereof, a peptide, a lipid, a fatty acid, a carbohydrate, and a small molecule.

In some embodiments, the VWF binding agent comprises a nucleic acid sequence selected from the group consisting of SEQ ID Nos.: 4-6 and variants thereof, and wherein the reversal agent comprises a nucleic acid sequence of SEQ ID No.: 10 or variant thereof.

As a non-limiting example, the method of treating, preventing, or preventing the progression of, or alleviating thrombosis associated with a clinical condition in a patient comprises administrating to the patient an effective amount of a VWF binding agent comprising the nucleic acid sequence of SEQ ID No.: 6 (BT200) or variant thereof; and administering to the patient an effective amount of a reversal agent comprising the nucleic acid sequence presented by SEQ ID No.: 10 (BT101) or variant thereof.

In some embodiments, the amount of the reversal agent is based on the amount of the VWF binding agent previously administered and the ratio of the reversal agent and the binding agent is based on a desired reduction in the activity of the VWF binding agent. In some examples, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some embodiments, the activity of the VWF binding agent is reversed by the reversal agent by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In another aspect, the present disclosure provides methods for treating and/or preventing a clinical condition associated with elevated levels of VWF in a patient comprising: administrating to the patient a therapeutically effective amount of a VWF binding agent comprising a nucleic acid sequence that binds to and inhibits the activity of VWF; and administering to the patient a therapeutically effective amount of a reversal agent that reverses the effect of the VWF binding agent and that comprises a second nucleic acid sequence complementary to the sequence or a portion of the sequence of the VWF binding agent, wherein the reversal agent is administered when the levels of plasma VWF need to be increased in the subject receiving the treatment of the VWF binding agent and compositions thereof.

In some embodiments, the clinical condition associated with elevated levels of VWF comprises systemic lupus erythematosus (SLE), first ischemic stroke, secondary stroke, TIA, silent stroke, a cardiovascular disease, diabetic disease, and cancer.

In some embodiments, the VWF binding agent is an aptamer comprising a nucleic acid sequence that binds to VWF and the reversal agent is an antidote of the VWF aptamer, which comprising a complementary sequence of the nucleic acid sequence of the VWF binding aptamer.

In some embodiments, the VWF binding agent is a VWF binding aptamer comprises the nucleic acid sequence presented by SEQ ID No.: 3, or variant thereof; and the reversal agent comprises the nucleic acid sequence presented by SEQ ID No.: 9, or variant thereof.

In some embodiments, the VWF binding agent and its reversal agent may include at least one chemical modification.

In some embodiments, the VWF binding agent and its reversal agent include at least one nucleotide modification with 2'-O-methyl modification.

In Some embodiments, the VWF binding agent is further modified with a conjugate selecting from the group consisting of a polymer (e.g., a PEG polymer), a protein, an antibody or variant thereof, a peptide, a lipid, a fatty acid, a carbohydrate, and a small molecule.

In some embodiments, the reversal agent is modified with a conjugate selecting from the group consisting of a PEG polymer, a protein, an antibody or variant thereof, a peptide, a lipid, a fatty acid, a carbohydrate, and a small molecule.

In some embodiments, the VWF binding agent comprises a nucleic acid sequence selected from the group consisting of SEQ ID Nos.: 4-6 and variants thereof, and wherein the reversal agent comprises a nucleic acid sequence of SEQ ID No.: 10 or variant thereof.

In one preferred embodiment, the method of treating and/or preventing a clinical condition associated with elevated levels of VWF in a patient comprises administrating to the patient an effective amount of a VWF binding agent comprising the nucleic acid sequence of SEQ ID No.: 6 (BT200) or variant thereof; and administering to the patient an effective amount of a reversal agent comprising the nucleic acid sequence presented by SEQ ID No.: 10 (BT101) or variant thereof.

In some embodiments, the amount of the reversal agent is based on the amount of the VWF binding agent previously administered and the ratio of the reversal agent and the binding agent is based on a desired reduction in the activity of the VWF binding agent. In some examples, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some embodiments, the activity of the VWF binding agent is reversed by the reversal agent by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In further another aspect, the present disclosure provides methods of modulating VWF activity in a blood circulatory system comprising introducing to the circulatory system an effective amount of a VWF binding agent having a nucleic acid sequence that binds to and inhibits the activity of VWF, and introducing to the circulatory system an effective amount of a reversal agent that sequesters/reverses the effects of the VWF binding agent and that includes a nucleic acid sequence complementary to the sequence or a portion of the sequence of the VWF binding agent. The introduction of the reversal agent is done after the administering the VWF binding agent.

In some embodiments, the VWF binding agent is an aptamer comprising a nucleic acid sequence that binds to VWF and the reversal agent is an antidote of the VWF aptamer, which comprising a complementary sequence of the nucleic acid sequence of the VWF binding aptamer.

In some embodiments, the VWF binding agent is a VWF binding aptamer comprises the nucleic acid sequence presented by SEQ ID No.: 3, or variant thereof; and the reversal agent comprises the nucleic acid sequence presented by SEQ ID No.: 9, or variant thereof.

In some embodiments, the VWF binding agent and its reversal agent may include at least one chemical modification.

In some embodiments, the VWF binding agent and its reversal agent include at least one nucleotide modification with 2'-O-methyl modification.

In Some embodiments, the VWF binding agent is further modified with a conjugate selecting from the group consisting of a polymer (e.g., a PEG polymer), a protein, an antibody or variant thereof, a peptide, a lipid, a fatty acid, a carbohydrate, and a small molecule. As non-limiting examples, the VWF binding agent may be conjugated with a PEG polymer or a fatty acid.

In some embodiments, the reversal agent is modified with a conjugate selecting from the group consisting of a PEG polymer, a protein, an antibody or variant thereof, a peptide, a lipid, a fatty acid, a carbohydrate, and a small molecule.

In some embodiments, the VWF binding agent comprises a nucleic acid sequence selected from the group consisting of SEQ ID Nos.: 4-6 and variants thereof, and wherein the reversal agent comprises a nucleic acid sequence of SEQ ID No.: 10 or variant thereof.

In one preferred embodiment, the method of modulating VWF activity in a blood circulatory system comprising introducing to the circulatory system an effective amount of a VWF binding agent comprising the nucleic acid sequence presented by SEQ ID No.: 6 (BT200) or variant thereof; and introducing to the circulatory system an effective amount of a reversal agent comprising the nucleic acid sequence presented by SEQ ID No.: 10 (BT101) or variant thereof, wherein the introduction of the reversal agent is done after the administering the VWF binding agent, and wherein the reversal agent sequesters/reverses the effects of the VWF binding agent.

In some embodiments, the amount of the reversal agent is based on the amount of the VWF binding agent previously administered and the ratio of the reversal agent and the binding agent is based on a desired reduction in the activity of the VWF binding agent. In some examples, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some embodiments, the activity of the VWF binding agent is reversed by the reversal agent by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In further another embodiment, the present disclosure provides methods of reversing the antithrombotic effect of a VWF binding agent in a patient, comprising administering to the patient a reversal agent in amount sufficient to effect said reversal, wherein the patient is previously administered to an effective amount of the VWF binding agent comprising a nucleic acid sequence that binds to and inhibits VWF activity.

In some embodiments, the VWF binding agent includes the nucleic acid sequence presented by SEQ ID No.: 3, or variant thereof. The reversal agent comprises the nucleic acid sequence presented by SEQ ID No.: 9, or variant thereof.

In some embodiments, the VWF binding agent and the reversal agent include at least one nucleotide modification with 2'-O-methyl modification. The VWF binding agent and its reversal agent may be further modified with a conjugate selecting from the group consisting of a PEG polymer, a protein, an antibody or variant thereof, a peptide, a lipid, a fatty acid, a carbohydrate, and a small molecule. As non-limiting examples, the VWF binding agent may be conjugated with a PEG polymer or a fatty acid.

In some embodiments, the VWF binding agent comprises a nucleic acid sequence selected from the group consisting of SEQ ID Nos.: 4-6 and variants thereof, and wherein the reversal agent comprises a nucleic acid sequence of SEQ ID No.: 10 or variant thereof.

In one preferred embodiment, the method of reversing the antithrombotic effect of a VWF binding agent in a patient comprising administering to the patient an effective amount of a reversal agent comprising the nucleic acid sequence presented by SEQ ID No.: 10 (BT101) or variant thereof, which sequesters/reverses the effects of the VWF binding agent comprising the nucleic acid sequence presented by SEQ ID No.: 6 (BT200) or variant thereof.

In some embodiments, the amount of the reversal agent is based on the amount of the VWF binding agent previously administered and the ratio of the reversal agent and the binding agent is based on a desired reduction in the activity of the VWF binding agent. In some examples, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some embodiments, the activity of the VWF binding agent is reversed by the reversal agent by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

BT200 is a PEGylated synthetic RNA oligonucleotide. In addition to PEGylation, BT200 contains a modified phosphorothioate backbone to increase in vivo stability to enable a convenient clinical dosing schedule.

In accordance with the present disclosure, the VWF binding agent may inhibit the interaction between VWF and Factor VIII, the VWF-platelet interaction and/or the VWF-erythrocyte interaction. The reversal agent can reverse the inhibitory effect induced by the VWF binding agent.

In another aspect of the present disclosure, a pharmaceutical composition comprising a reversal agent having a nucleic acid sequence of SEQ ID No.: 9 or variant thereof, and a pharmaceutically acceptable carrier, is provided. In some embodiments, the reversal agent includes at least one nucleotide modification with 2'-O-methyl modification. The reversal agent may be further modified with a conjugate selecting from the group consisting of a PEG polymer, a protein, an antibody or variant thereof, a peptide, a lipid, a fatty acid, a carbohydrate, and a small molecule.

As a non-limiting example, the pharmaceutical composition comprises a reversal agent comprises the nucleic acid sequence presented by SEQ ID No.: 10 (BT101) or variant thereof.

In some embodiments, a VWF activity regulation composition composed of a VWF binding agent that binds to and inhibits VWF activity and a reversal agent that neutralizes/reverses the effect of the VWF binding agent, is provided. In accordance, the VWF binding agent is administered to a subject in need first to inhibit VWF activity, and the reversal nucleic acid sequence is administered to the subject when a condition that needs to increase VWF activity arises.

In some embodiments, the VWF binding agent comprises a nucleic acid sequence of SEQ ID No.: 3 or variant thereof, and the reversal agent comprises a nucleic acid sequence of SEQ ID No.: 9 or variant thereof.

In some embodiments, the VWF binding agent and the reversal agent includes at least one nucleotide modification with 2'-O-methyl modification. The VWF binding agent and/or the reversal agent may be further modified with conjugate selecting from a PEG polymer, a protein, an antibody or variant thereof, a peptide, a lipid, a fatty acid, a carbohydrate, and a small molecule.

As non-limiting examples, the VWF activity regulation composition is composed of a VWF binding agent comprising a nucleic acid sequence selected from the group consisting of SEQ ID Nos.: 4-6 and variants thereof and a reversal agent comprising a nucleic acid sequence of SEQ ID No.: 10 or variant thereof.

In another aspect of the present disclosure, a kit for therapeutic use is provided, including 1) a VWF binding agent comprising a nucleic acid sequence selected from the group consisting of SEQ ID Nos.: 3 to 6 and variants thereof; 2) a reversal agent that reverses the effect of the VWF binding agent and that includes a nucleic acid sequence complementary to the sequence or a portion of the sequence of the VWF binding agent; and 3) an introduction for use of the kit.

In some embodiments, the kit includes the VWF binding agent comprising a nucleic acid sequence selected from the group consisting of SEQ ID Nos.: 3-6 and variants thereof, and the reversal agent comprising a nucleic acid sequence selected from the group consisting of SEQ ID Nos.: 9-10 and variants thereof. presented by SEQ ID No.: 10 (BT101) or variant thereof.

In one example, the kit for therapeutic use includes a VWF binding agent comprising the nucleic acid sequence presented by SEQ ID No.: 6 (BT200) or variant thereof, and a reversal agent comprising the nucleic acid sequence presented by SEQ ID No.: 10 (BT101) or variant thereof.

In some embodiments, the kit further comprises an assay part for measuring VWF levels.

DETAILED DESCRIPTION OF THE DISCLOSURE

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure. Unless defined otherwise, all technical and scientific terms used herein have the same meaning as commonly understood by one of ordinary skill in the art to which this disclosure belongs. In the case of conflict, the present description will control.

The present disclosure relates to agents and methods for preventing and treating thrombosis with rapid and predictable reversal of the anti-thrombotic effects induced by anti-thrombotic drugs when there is a potential hemorrhagic risk in a patient in need. Particularly, the thrombus formation is induced by VWF mediated platelet adhesion and aggregation. The anti-thrombotic agent is an aptamer that binds to and inhibits VWF mediated thrombosis, particularly VWF mediated platelet adhesion and aggregation. The inhibition of VWF function induced by an anti-VWF aptamer is reversed and neutralized by an antidote of the anti-VWF aptamer. The reversal can rapidly restore the function of VWF, e.g., initiating thrombus formation.

Definitions

To more clearly and concisely describe the subject matter of the claimed disclosure, the following definitions are provided for specific terms, which are used in the following description and the appended claims. Throughout the specification, exemplification of specific terms should be considered as non-limiting examples.

The present disclosure relates to nucleic acid agents that modulate VWF, particularly aptamers that bind to VWF and their antidotes. As used herein, an "aptamer" is a biomolecule that binds to a specific target molecule and modulates the target's activity, structure, or function. Aptamers often are referred to as "chemical antibodies," having similar characteristics as antibodies. An aptamer can be nucleic acid or amino acid based, i.e., either a nucleic acid aptamer or peptide aptamer. Nucleic acid aptamers have specific binding affinity to target molecules through interactions other than classic Watson-Crick base pairing. Nucleic acid aptamers are capable of specifically binding to selected targets and, through binding, block their targets' ability to function. Aptamers of the present disclosure are synthetic oligonucleotides. A typical nucleic acid aptamer is approximately 10-15 kDa in size, binds its target with sub-nanomolar affinity, and discriminates against closely related targets. A target of a nucleic acid aptamer may be but is not limited to, a protein, a nucleic acid molecule, a peptide, a small molecule and a whole cell.

Nucleic acid aptamers may be ribonucleic acid (RNA), deoxyribonucleic acid (DNA), or mixed ribonucleic acid and deoxyribonucleic acid (DNA/RNA hybrid). Aptamers may be single stranded. A suitable nucleotide length for an aptamer ranges from about 15 to about 100 nucleotide (nt), and in various other preferred embodiments, 15-30 nt, 20-25 nt, 20-45 nt, 30-100 nt, 30-60 nt, 25-70 nt, 25-60 nt, 40-60 nt, 25-40 nt, 30-40 nt, any of 22, 23, 24, 25, 26, 27, 28, 29, 30, 31, 32, 33, 34, 35, 36, 37, 38, 39 or 40 nt, or 30-50 nt, or 40-70 nt in length. However, the sequence can be designed with sufficient flexibility such that it can accommodate interactions of aptamers with targets.

Aptamers can be generated against a target molecule (e.g., VWF) using a process called either in vitro selection (Ellington and Szostak; In vitro selection of RNA molecules that bind specific ligands. Nature. 1990; 346:818-822) or SELEX (Tuerk and Gold, Systematic evolution of ligands by exponential enrichment: RNA ligands to bacteriophage T4 DNA polymerase; *Science,* 1990, 249:505-510). This method allows the in vitro evolution of nucleic acid molecules with highly specific binding to target molecules. The SELEX method is described in, for example, U.S. Pat. Nos.

7,087,735, 5,475,096 and 5,270,163; the contents of each of which are incorporated by reference herein in their entirety. Nucleic acid aptamers can be synthesized using methods well-known in the art. For example, the disclosed aptamers may be synthesized using standard oligonucleotide synthesis technology known in the art.

As used herein, the terms "nucleic acid," "polynucleotide," "oligonucleotide" are used interchangeably. A nucleic acid molecule is a polymer of nucleotides consisting of at least two nucleotides covalently linked together. A nucleic acid molecule is a DNA (deoxyribonucleotide), an RNA (ribonucleotide), as well as a recombinant RNA and DNA molecule or an analogue of DNA or RNA generated using nucleotide analogues. The nucleic acids may be single stranded or double stranded, linear or circular. The term also comprises fragments of nucleic acids, such as naturally occurring RNA or DNA which may be recovered using the extraction methods disclosed, or artificial DNA or RNA molecules that are artificially synthesized in vitro (i.e., synthetic polynucleotides). Molecular weights of nucleic acids are also not limited, may be optional in a range from several base pairs (bp) to several hundred base pairs, for example from about 2 nucleotides to about 1,0000 nucleotides, or from about 10 nucleotides to 5,000 nucleotides, or from about 10 nucleotides to about 1,000 nucleotides.

The term "nucleotide" refers to the monomer of nucleic acids, a chemical compound comprised of a heterocyclic base, a sugar and one or more phosphate groups. The base is a derivative of purine and pyrimidine and the sugar is a pentose, either deoxyribose or ribose.

As used herein, the term "modification" refers to the technique of chemically reacting a nucleic acid, e.g., an RNA molecule, a DNA molecule, an aptamer, and an oligonucleotide, with chemical reagents. A nucleic acid may be modified in the base moiety, sugar moiety or phosphate backbone. The modifications include, but are not limited to, 2'-position sugar modifications, 5-position pyrimidine, modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping. The nucleic acid molecule may also be modified by conjugation to a moiety having desired biological properties. Such moiety may include, but is not limited to, compounds, peptides and proteins, carbohydrates, antibodies, enzymes, polymers, drugs and fluorophores. In some examples, the polynucleotide is conjugated to a lipophilic compound such as cholesterol, dialkyl glycerol, diacyl glycerol, or a non-immunogenic, high molecular weight compound or polymer such as PEG (polyethylene glycol) or other water soluble pharmaceutically acceptable polymers including, but not limited to, polyaminoamines (PAMAM) and polysaccharides such as dextran, or polyoxazolines (POZ). The modifications may be intended, for example, to increase the in vivo stability of nucleic acid molecules or to enhance or to mediate delivery of the molecules.

As used herein, the term "antidote" refers to a DNA or RNA oligonucleotide capable of hybridizing via base complementarity to the aptamer resulting in a secondary structure change of the aptamer and thus preventing and even reversing the binding of an aptamer to its target. An antidote may include a nucleotide sequence having 50%, 55%, 60%, 65%, 70%, 75%, 80%, 85%, 90%, 91%, 92%, 93%, 94%, 95%, 96%, 97%, 98%, 99%, or 100% sequence identity to a sequence reverse complementary to and/or capable of hybridizing to at least 5, 6, 7, 8, 9, 10, 11, 12, 13, 14, 15, 16, 17, 18, 19, or 20 nucleotides present in the aptamers. Those skilled in the art will appreciate that the sequences would be altered to include thymines in place of the uracils when in a DNA form. The antidote can change the conformation of the aptamer to reduce the target binding capacity of the aptamer by 10 to 100%, 20 to 100%, 30 to 100%, 40 to 100%, 50 to 100%, 60 to 100%, 70 to 100%, 80-100%, 25%, 40%, 45%, 50%, 55%, 60%, 65%, 70%, 75%, 80%, 85%, 90%, 95% or 100%, or any percentage in the range between 10 and 100% under physiological conditions. The antidote can also form a three-dimensional structure with binding activity to a target molecule. This target can be the same or different from the target of the aptamer.

In some embodiments, the antidote comprises a single oligonucleotide sequence capable of hybridizing via base complementarity to the aptamer resulting in a secondary structure change of the aptamer and thus preventing and even reversing the binding of an aptamer to its target. In other embodiments, the antidote comprises a multiplicity of different oligonucleotide sequences capable of hybridizing via base complementarity to different portions of the aptamer resulting in a secondary structure change of the aptamer and thus preventing and even reversing the binding of an aptamer to its target. In some cases, the multiplicity of different oligonucleotide sequences comprises 2, 3, 4, or more different oligonucleotide sequences. The multiplicity of different oligonucleotide sequences may be a portion of the same oligonucleotide or different oligonucleotides. Different oligonucleotides may be covalently or non-covalently linked by chemistries described above for linking aptamers to sorting labels or other aptamers.

Antidotes can be generated against aptamers by screening complementary oligonucleotides by methods known in the art. The antidotes disclosed herein may be synthesized using methods known in the art. For example, the disclosed antidotes may be synthesized using standard oligonucleotide synthesis technology commercially available.

As used herein, the term "complementary" generally refers to specific nucleotide duplexing to form canonical Watson-Crick base pairs, as is understood by those skilled in the art. For example, two nucleic acid strands or parts of two nucleic acid strands are said to be complementary or to have complementary sequences in the event that they can form a perfect base-paired double helix with each other. The term "hybridization" refers to non-covalent bonding through base pairings between A and T, and G and C.

As used herein, the term "thrombosis" refers to the formation of a blood clot (i.e., thrombus) inside a blood vessel, which obstructs the blood flow through the circulatory system. The blood clots are mainly formed by platelets and blood proteins such as fibrin. Thrombosis may occur in veins (venous thrombosis) (e.g., deep venous thrombosis (DVT) or in arteries (arterial thrombosis) (e.g., myocardial infarction and ischemic stroke), or cardiac chambers. Thrombosis can result in e.g., strokes, heart attacks, and pulmonary embolism. Thrombus is structured by numerous elements, including endothelial cells, plasma proteins and shear stress alteration. Thrombus formation results from a confluence of two major physiologic pathways, one involving coagulation proteins and the other involving platelets. The platelet-mediated thrombogenesis is predominant in arterial circulation (Fuster and Chesebro, Antithrombotic therapy: role of platelet-inhibitor drugs. I. Current concepts of thrombogenesis: role of platelets. (first of three parts).

*Mayo Clin Proc*. 1981;56 (2): 102-112; and Vermylen et al., Role of platelet activation and fibrin formation in thrombogenesis. *J Am Coll Cardiol*. 1986;8 (6 Suppl B): 2B-9B). The platelet mediated thrombogenesis involves a sequence of steps of adhesion, activation and aggregation (Ruggeri and Mendolicchio. Adhesion mechanisms in platelet function. *Circ Res*. 2007; 100 (12): 1673-1685). The platelet adhesion is often triggered by damaged or denuded vascular endothelium which causes subendothelial collagen to expose to the bloodstream. Circulating VWF molecules can bridge the exposed collagen on the endothelial vessel wall and platelet, recruiting blood platelets to the damaged sites which aggregate to form thrombus to block bleeding.

As used herein, the term "stroke" refers to a clinical condition in which a brain attack which cuts off vital blood flow and oxygen to the brain. The insufficient blood supply may result from a blocked artery (ischemic stroke) or the leaking or bursting of a blood vessel (hemorrhagic stroke). Approximately 80% of all strokes are ischemic strokes caused by thrombosis, emboli or systemic hypo-perfusion. In the context of the present disclosure, the term "stroke" refers to all types of stroke, including primary stroke, secondary stroke, transient ischemic attack (TIA), and silent stroke.

The term "transient ischemic attack (TIA)" (also referred to as "mini stroke") is a brief interruption of blood flow to the brain that causes temporary stroke-like symptoms and is caused by the changes in the blood supply to a particular area of the brain, resulting in brief neurologic dysfunction that persists, by definition, for less than 24 hours; if symptoms persist then it is categorized as a stroke. Patients diagnosed with a TIA could have a warning for an approaching stroke. If the time period of blood supply impairment lasts more than a few minutes, the nerve cells of that area of the brain die and cause permanent neurologic deficit. One third of the people with TIA later have recurrent TIAs and one third have a stroke due to permanent nerve cell loss.

As used herein, the term "therapeutically effective amount" refers to the amount of the compound that is sufficient to result in a therapeutic response. In connection with the present disclosure, the term "therapeutically effective amount" may refer to the amount of an anti-VWF aptamer and/or its reversal agent that is sufficient to result in a therapeutic response. A therapeutic response may be any response that a user (e.g., a clinician) will recognize as an effective response to the therapy. The exact amount required will vary from subject to subject, depending on the species, age, and general condition of the subject, the particular therapeutic agent, its mode and/or route of administration, and the like. It will be understood, however, that the total daily usage of the compounds and compositions of the present invention can be decided by an attending physician within the scope of sound medical judgment. Thus, a therapeutic response will generally be an amelioration of one or more symptoms of a disease or disorder such as stroke and TIA. In some examples, the effective amount can be administered in one or more administrations, applications or dosages.

As used herein, the terms "pharmaceutical composition" and "pharmaceutical formulation" refer to the combination of an active compound with a pharmaceutically acceptable carrier or excipient, inert or active, making the composition suitable for diagnostic or therapeutic use in vitro, in vivo or ex vivo. In the context of the present disclosure, the active compound may be one or more compound that can be used to treat or prevent stroke, such as an agent that regulates VWF function, e.g., an anti-VWF aptamer and a corresponding reversal agent.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. In some examples, the compositions and formulations also can include stabilizers and preservatives.

As used herein, the term "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans, or generally recognized as safe for use in parenteral products.

As used herein, the terms "treating," "treatment" and "to treat" and grammatical variations thereof, refer to administering to a subject a pharmaceutical composition, such that at least one symptom of a disease is reversed, cured, alleviated or decreased. In the context of the present disclosure, the terms "to treat," "treating," "treatment" and grammatical variations thereof include reducing one or more of: the size of a neural infarct, neural edema, neural inflammation, vision disturbances, seizures, incontinence, paralysis, pain, fatigue, vascular dementia, aphasia, short-term memory loss, long-term memory loss, depression, and pseudobulbar affect as compared with prior to treatment of the subject or as compared with the incidence of such symptom in a general or stroke or TIA or silent ischemia patient population.

As used herein, the terms "prevent," "preventing," and "prevention" and grammatical variations thereof are used interchangeably. These terms refer to a method of partially or completely delaying or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms.

As used herein, the terms "subject," "individual" and "patient" are used interchangeably, and refer to a vertebrate, preferably a mammal, more preferably a human. Mammals include, but are not limited to, murine, simians, humans, farm animals, sport animals, and pets.

As used herein, the term "ratio" refers to a dimensionless number when two quantities are measured in the same unit, the unit may be mass, volume, or concentration. In some examples, the quantities of the VWF binding agent and the reversal agent may be measured in moles. In other examples, the quantities of the VWF binding agent and the reversal agent may be measured by dose unit. In accordance with the present disclosure, the ratio of the VWF agent and its reversal agent is from about 20:1 to about 1:20 in moles, or about 10:1 to about 1:10 in moles, or about 5:1 to about 1:5 in moles. In one example, the ratio of the VWF binding agent and its reversal agent is at 1:1 in moles, or at 1:1.5 in moles, or at 1:2 in moles, or at 1:3 in moles, or at 1:4 in moles, or at 1:5 in moles, or at 1:10 in moles.

VWF and Pathological Conditions

VWF Function von Willebrand factor (VWF) is a glycoprotein circulating in blood, particularly in the arterial circulation. Human VWF preproprotein synthesized mainly within endothelial cells and megakaryocytes (GeneBank Ref. No. NP_000543.2; SEQ ID No.: 1) (encoded by cDNA: GeneBank Ref. No. NM_000552.3; SEQ ID No.: 2) is further processed to be a mature polypeptide of 2020 AA containing multiple domains arranged in the following order: D'-D3-A1-A2-A3-D4-C1-$C_2$-$C_3$-C4-C5-C6-CK; each of the multiple subdomains has different functions (Hassan and Saxena, Structure and function of von Willebrand Factor, *Blood Coagul. Fibrinolysis,* 2012, 23 (1): 11-22). Mature VWF forms VWF multimers through extensive intracellular modifications. Ultra-large VWF multimers are cleaved by ADAMTS13 into smaller multimers that circulate inactively in a coiled conformation in plasma.

VWF plays a pivotal role in hemostasis and thrombosis. VWF is a mediator of platelet adhesion and aggregation, playing a central role in the initiation of platelet mediated thrombosis, as well as blood coagulation. VWF is also a carrier of Factor VIII (FVIII) (a clotting protein), as a chaperon, to protect FVIII from proteolytic inactivation, ultimately delivering it to sites of vascular damage. Normally large multimer forms of VWF are mainly stored in Weibel-Palade bodies and granules of endothelial cells and platelets, respectively. Upon vascular injury, activated VWF under shear stress, mediates the anchoring of platelets to the sub-endothelium to form a platelet plug, thereby blocking bleeding.

Vascular injury triggers a rapid diversion in the blood flow and shear rate leading to the initial attachment of platelet at the site of injury, which then activates VWF. Increased levels of active VWF in the blood recruit further platelets to initiate platelet adhesion, aggregation and stabilization. The platelets and thrombi thereby seal the damaged vascular wall to prevent blood leakage. During this process, activated VWF binds to the exposed collagen on the damaged and denuded endothelium through the A3 domain and to platelet glycoprotein GPIba receptor through its A1 domain; the binding is induced by fluid shear force which can unfold coiled VWF multimers and expose VWF A1 domain to GPIba (Schneider et al., Shear-induced unfolding triggers adhesion of von Willebrand factor fibers. *Proc Nat Acad Sci USA*. 2007; 104 (19): 7899-7903). The VWF-GPIba interaction is an essential adhesive interaction triggering platelet activation and cell aggregation.

Plasma levels of VWF have a continuous and wide distribution in healthy populations. Quantitative deficiencies (low levels) of plasma VWF (e.g., <50%) are associated with an increased risk for bleeding while high plasma levels of VWF (e.g., >150%) increase the risk for thrombosis (e.g., higher risk for venous thromboembolic disease, stroke, transient ischemic attack (TIA), silent ischemia, myocardial infarction and coronary artery disease).

Qualitative and quantitative deficiencies of VWF cause von Willebrand disease (VWD) that is the most common inherited bleeding disorder in humans, and venous thromboembolic disease (VTE).

There are a few thrombotic disorders that are directly attributed to increased levels of VWF, including TTP, which is caused by high levels of VWF due to the deficiencies of VWF cleavage enzyme ADAMT13; hemolytic uremic syndrome (HUS) that results in excessive release of VWF from kidney vascular endothelial cells. Elevated levels of VWF are positively associated with stroke and arterial thrombotic disorders as discussed herein.

VWF and Thrombotic Diseases

As used herein, the terms "thrombotic disease" refers to a group of clinical conditions in which thrombi block the blood circulation. The thrombi may be in veins, arteries and heart.

Stroke

VWF has been implicated as a critical indicator/risk factor for ischemic stroke. The high levels of VWF have a close association with stroke in patients. Many studies have demonstrated that plasma levels of VWF are associated with the risk of stroke in the general population (e.g., reviewed by Buchtele, N. et al., Targeting von Willebrand Factor in ischaemic stroke: focus on clinical evidence. *Thrombosis and Haemostasis* 2018; 118 (6): 959-978). The importance of VWF as a risk factor for stroke occurrence and mortality in humans recently also stimulated experimental studies in models of acute stroke (De Meyer et al., Binding of von Willebrand factor to collagen and glycoprotein Iba, but not to glycoprotein IIb/IIIa, contributes to ischemic stroke in mice. *Arterioscler Thromb Vasc Biol.* 2010; 30:1949-1951). VWF's contribution to arterial thrombi formed under shear stress and the resistance of VWF containing thrombi to therapeutic dissolution are illustrated in animal models of acute ischemic stroke as well (Le Behot et al., GpIbα-VWF blockade restores vessel patency by dissolving platelet aggregates formed under very high shear rate in mice. *Blood,* 2014; 123 (21): 3354-3363). VWF's role in platelet thrombogenesis at sites of arterial vascular injury and functional "silence" makes it a target or primary and secondary stroke prevention, and for stroke treatment as well.

The positive association between baseline VWF levels and the risk of stroke occurrence (i.e., first-time ever stroke) is shown in several prospective population-based cohort studies (Rotterdam study), indicating that increasing VWF levels are associated with a significant increase in the risk of stroke. These findings support that VWF levels, and the VWF-modifying enzyme ADAMTS13 play an important role in the development of first-ever stroke.

In addition to the association between total VWF levels and the occurrence of a first ischemic stroke, studies also indicate high plasma levels of VWF as a strong predictor of stroke (Roldán et al., Correlation of plasma von Willebrand factor levels, an index of endothelial damage/dysfunction, with two point-based stroke risk stratification scores in atrial fibrillation. *Thromb Res.* 2005; 116:321-325; Lip et al., Additive role of plasma von Willebrand factor levels to clinical factors for risk stratification of patients with atrial fibrillation. *Stroke.* 2006; 37:2294-2300; and Carter et al., variables for mortality after acute ischemic stroke. *Stroke.* 2007; 38:1873-1880).

VWF levels are heightened as well in patients experiencing recurrent cardiac events after ischemic stroke (e.g., Pedersen et al., Haemostatic biomarkers are associated with long-term recurrent vascular events after ischaemic stroke, *Thromb Haemost.* 2016; 116 (3): 537-543; and Williams et al., Genetic drivers of von Willebrand factor levels in an ischemic stroke population and association with risk for recurrent stroke, *Stroke,* 2017; 48 (6): 1444-1450).

The VWF levels are increased particularly in certain subtypes of ischemic stroke, e.g., large-vessel disease (LVD), cardioembolic (CE) stroke and cryptogenic stroke. For example, Hanson reported that VWF levels are significantly higher in large artery atherosclerosis (LAA) subtype stroke than in small vessel disease (Hanson et al., Plasma levels of von Willebrand factor in the etiologic subtypes of ischemic stroke. *J Thromb Haemost* 2011; 9 (02): 275-281; the contents of which are herein incorporated by reference in their entirety). The LAA sub-type of stroke could be particularly sensitive to a VWF blocking strategy. Menih et al. also found that VWF plasma levels are associated with large vessel and cardioembolic but not small vessel stroke (Menih et al., Clinical role of von Willebrand factor in acute ischemic stroke. *Wien Klim Wochmeschr.,* 2017; 129 (13-14): 491-496).

The associations between VWF levels and the development of atherosclerotic-driven stroke are also confirmed in longitudinal assessments. Increased VWF levels VWF are also associated with transient ischemic attack (TIA) (Greisenegger et al., Biomarkers and mortality after transient ischemic attack and minor ischemic stroke: population-based study, *Stroke;* 2015; 46 (3): 659-666) and silent ischemia.

Other Thrombotic Diseases

Increased levels of VWF are also associated with a variety of other chronic or acute pathological conditions which involve thrombotic pathology, such as diabetes, vascular parkinsonism, Alzheimer's' disease, vascular dementia, traumatic brain injury, acute lung injury, and preeclampsia, as well as sepsis, and various infectious diseases including HIV, malaria, scrub typhus and dengue virus infection. Kraft et al, reported that in a case-control study, patients with chronic cerebrovascular disease (CCD) have significantly higher VWF levels (Kraft et al., Von Willebrand factor regulation in patients with acute and chronic cerebrovascular disease: a pilot, case-control study. *Plos One,* 2014; 9 (6): e99851).

VWF and Non-Thrombotic Diseases

VWF can negatively impact the regulation of angiogenic process in endothelial cells. In VWF deficient endothelial cells in vitro and in vivo, angiogenic activities are increased. Lack of VWF causes enhanced vascularization, both constitutively and following ischemia (e.g., reviewed by Randi et el., von Willebrand factor regulation of blood vessel formation. *Blood,* 2018; 132 (2): 132-140).

Elevated VWF levels in patients with inflammatory vascular disease are commonly observed. VWF mediated platelet interactions through the VWF-GPIbα axis contribute to the promotion of inflammation. VWF's role in inflammation highlights its importance in atherothrombosis which leads to ischemic stroke. Arteriosclerosis is a localized inflammatory process in which VWF multimers are released under shear stress, trapping platelets and recruiting other immune cells. Increased VWF levels were associated with various arthritis including giant cell and rheumatoid arthritis, vasculitis, and systemic lupus disease.

VWF levels are increased in diabetic patients (Peng et al., Plasma levels of von Willebrand factor in type 2 diabetes patients with and without cardiovascular diseases: A meta-analysis, *Diabetes Metab. Res. Rev.;* 2019; May 30: e3193)

VWF also contributes to cancer metastasis, like apoptosis of tumor cells (e.g., Terraube et al., Role of von Willebrand factor in tumor metastasis, *Thromb Res,* 2007; 120 (Suppl. 2): S64-70).

VWF as Therapeutic Target

The association of elevated levels of thrombosis make VWF a promising target for treatment and/or prevention of thrombotic disorders. As VWF plays a critical role in both thrombotic and bleeding events, an elevated plasma level of VWF may relate to a thrombotic occurrence but a decreased plasma level may point to a bleeding condition. The levels of VWF in the plasma need to be tightly regulated in a variety of clinical conditions. In clinical conditions associated with thrombi, it is proposed that inhibiting VWF mediated platelet adhesion and aggregation will significantly reduce and prevent thrombus formation. Inhibition of VWF can be achieved by antibodies, nanobodies, aptamers and other inhibitory agents.

Similar to other anti-thrombotic drugs, an adverse event associated with these drugs targeting VWF is prone to bleeding, causing in severe cases death. The drugs targeting VWF-mediated platelet adhesion and aggregation points to a higher bleeding risk profile though a higher efficacy compared with other anti-thrombotic drugs.

In accordance with the present disclosure, VWF targeting agents include aptamers that bind to and inhibit VWF mediated platelet adhesion and aggregation, thereby inhibiting thrombus formation. The present disclosures also provide antidotes of anti-VWF aptamers to rapidly reverse the inhibitory effect to VWF induced by these anti-VWF aptamers, when bleeding is an issue. The antidotes act as reversal agents of the VWF binding agents (i.e., anti-VWF aptamers). Dosages, administrations and methods of use of these aptamer-antidote pairs to modulate VWF activities are disclosed herein.

Anti-VWF Aptamers

Agents and compositions that interfere VWF-mediated platelet adhesion and thrombus formation could have clinical benefit as a promising strategy in stroke treatment and prevention (De Meyer et al., von Willebrand factor: an emerging target in stroke therapy, *Stroke.* 2012; 43 (2): 599-606). Inhibitors of VWF-mediated thrombosis include antibodies, nanobodies, aptamers, recombinant inhibitory fragments (e.g., GPG-290) and other VWF antagonists (e.g., an antagonist derived from snake venom).

These VWF inhibitors may include but are not limited to ARC15015 and ARC1779, DNA/RNA aptamers targeting GP1bα-VWF; AJW200, a monoclonal antibody targeting GP1bα-VWF; rADAMTS13, a recombinant ADAMTS13 targeting large VWF multimers; Anfibatide, a derivative from snake toxin targeting GP1bα-VWF; and Caplacizumab, a nano-body targeting GP1bα-VWF, and nanobodies ALX-0081 and ALX-0681 (reviewed by Buchtele et al., Targeting von Willebrand Factor in Ischaemic Stroke: Focus on Clinical Evidence; *Thromb Haemost,* 2018, 118 (6): 959-978; DTRI-031, a VWF aptamer by Nimijee et al., (Preclinical Development of a vWF Aptamer to Limit Thrombosis and Engender Arterial Recanalization of Occluded Vessels; *Mol. Ther.,* 2019; 27 (7): 1228-1241); the contents of each of which are incorporated herein by reference in their entirety).

Aptamers against VWF can bind to VWF to block interaction between VWF and GP1b receptor of platelets, thereby interfering platelet mediated adhesion and aggregation. The anti-VWF aptamers may also interfere the interaction between VWF and Factor VIII. Aptamers against VWF and derivatives thereof are referred to as "VWF binding agents."

In some embodiments, the VWF binding agent is an aptamer or a salt thereof comprising the nucleic acid sequence, 5'GCCAGGGACCUAAGACACAUGUCC-CUGGC-3' (SEQ ID No.: 3). In one embodiment, the VWF binding agent may be a synthetic polynucleotide comprising at least 21 contiguous nucleotides of SEQ ID No.: 3. Additionally, the synthetic polynucleotides may exhibit a double stranded region having at least 6 base pairs. While not wishing to be bound by theory, shorter double stranded regions of 5 base pairs or less may lead to the unraveling of the stem-loop structure at higher temperatures and the associated loss of affinity and functionality of the protective agents. In one embodiment, the double stranded region of 6 or more base pairs is at or near (e.g., within 1-10 nucleotides) the termini of the synthetic polynucleotide.

In some embodiments, the synthetic polynucleotide may comprise chemical modification e.g., in the base moiety (A, T, U, G or C), sugar moiety and/or phosphate backbone. In some aspects, the chemical structure and properties of the bases may be modified. Exemplary modified bases may include but are not limited to, 2'-O-Methoxy-ethyl Bases (2'MOE bases), 2' Fluoro bases, 2,6-Diaminopurine (2-Amino-dA), Dideoxycytidine (ddC), 2'-deoxyInosine (dI), Hydroxymethyl dC, Inverted dT, Iso-dG, Iso-dC, 5-Methyl deoxyCytidine (5-Methyl dC), 5-Nitroindole, 2-Aminopurine, 5-Bromo dU, and deoxy Uridine.

The anti-VWF aptamer may also be modified in the sugar.

It is contemplated by the present disclosure that the synthetic polynucleotide/aptamers described herein may also be modified by conjugation to a moiety having desired biological properties. In some embodiments, the VWF binding agents described herein may comprise conjugates. Such conjugates may include, but are not limited to, a naturally occurring substance or ligand, such as a protein (e.g., human serum albumin (HSA), low-density lipoprotein (LDL), high-density lipoprotein (HDL), or globulin), an antibody or variant thereof, a carbohydrate (e.g., a dextran, pullulan, chitin, chitosan, inulin, cyclodextrin or hyaluronic acid) and a lipid. In other embodiments, the conjugate may include a lipophilic compound such as a fatty acid, a polymer, small molecule, or peptide.

In some embodiments, the VWF binding agent is conjugated with a polymer such as a polyethylene glycol (PEG) polymer or derivatives thereof.

In some embodiments, the VWF binding agent is conjugated with a fatty acid moiety.

As used herein, the term "fatty acid" refers to a carboxylic acid (or organic acid), often with a long aliphatic tail, either saturated or unsaturated. Generally, fatty acids have a carbon-carbon bonded chain of at least 8 carbon atoms in length, more preferably at least 12 carbons in length. Most naturally occurring fatty acids have an even number of carbon atoms because their biosynthesis involves acetate which has two carbon atoms. The fatty acids may be in a free state (non-esterified) or in an esterified form such as part of a triglyceride, diacylglyceride, monoacylglyceride, acyl-CoA (thio-ester) bound or other bound form. The fatty acid may be esterified as a phospholipid such as a phosphatidylcholine, phosphatidylethanolamine, phosphatidylserine, phosphatidylglycerol, phosphatidylinositol or diphosphatidylglycerol forms.

In some embodiments, the VWF binding agents described herein may be conjugated to a saturated fatty acid. As used herein, the term "saturated fatty acids" do not contain any double bonds along the chain. In some embodiments, the saturated fatty acids do not contain any other functional groups along the chain. In some embodiments, the saturated fatty acids contain other functional groups along the chain. The term "saturated" refers to hydrogen, in that all carbons (apart from the carboxylic acid [—COOH] group) contain as many hydrogens as satisfied by valency.

In some embodiments, the VWF binding agents described herein may be conjugated to an unsaturated fatty acid. As used herein, the term "unsaturated fatty acids" are of similar form to saturated fatty acids, except that one or more alkene functional groups exist along the chain, with each alkene substituting a singly-bonded "—CH2—CH2—" part of the chain with a doubly-bonded "—CH═CH—" portion. The two next carbon atoms in the chain that are bound to either side of the double bond can occur in a cis or trans configuration.

In some embodiments, the VWF binding agents described herein may be conjugated to a monounsaturated fatty acid. In some embodiments, the VWF binding agents and/or reversal agents described herein may be conjugated to a polyunsaturated fatty acid. As used herein, the term "monounsaturated fatty acid" refers to a fatty acid which comprises at least 12 carbon atoms in its carbon chain and only one alkene group in the chain. As used herein, the term "polyunsaturated fatty acid" refers to a fatty acid which comprises at least 12 carbon atoms in its carbon chain and at least two alkene groups (carbon-carbon double bonds). In one embodiment, the long-chain polyunsaturated fatty acid is an @3 fatty acid, that is, having an unsaturation (carbon-carbon double bond) in the third carbon-carbon bond from the methyl end of the fatty acid.

Non-limiting examples of fatty acids include palmitic acid, lauric acid, myristic acid, undecylic acid, stearic acid, butyric acid, valeric acid, caproic acid, arachidic acid, behenic acid, capric acid, caprylic acid, carboceric acid, ceroplastic acid, cerotic acid, enanthic acid, geddic acid, heneicosylic acid, hentriacontylic acid, heptatriacontanoic acid, hexatriacontylic acid, lacceroic acid, lignoceric acid, margaric acid, melissic acid, montanic acid, nonacosylic acid, nonadecylic acid, nonatriacontylic acid, octatriacontylic acid, pelargonic acid, pentacosylic acid, pentadecylic acid, psyllic acid, stearic acid, tetracontylic acid, tricosylic acid, and tridecylic acid.

According to the nucleic acid aptamers provided by the present disclosure, terminal cap structures may also be incorporated to the 3' and/or 5' termini. Such structures include, but are not limited to, at least one inverted deoxythymidine or amino group (NH2). In one embodiment, the 3' cap is an inverted deoxythymidine cap. In another embodiment, the 3' cap is an amino group (NH2). In one embodiment, the 5' cap is an inverted deoxythymidine (idT) cap. In another embodiment, the 5' cap is an amino group (NH2). In some embodiments, the fatty acid moiety is conjugated to the 5' terminus of the nucleic acid aptamer. In some embodiments, the fatty acid moiety is conjugated to the 3' terminus of the nucleic acid aptamer.

In some embodiments, the fatty acid may be further connected to a linker. The term "linker" as used herein refers to a group of atoms (e.g., 10-1,000 atoms), molecule(s), or other compounds used to join two or more entities. Linkers may join such entities through covalent or non-covalent (e.g., ionic, or hydrophobic) interactions.

In some embodiments, the VWF binding agent is aptamer or a salt thereof comprising the structure: mGmCmC-mAmGmGmGmAmCmCmUmAmAmGmAmCmAmC-mAmUmGmUmCmCmC mUmGmGmC-idT (SEQ ID No.: 4) (BT99), where "idT" is an inverted deoxythymidine, "mN" is a 2'-O-Methyl containing residue.

In some embodiments, the VWF binding agent is an aptamer or a salt thereof comprising the structure: NH2-mGmCmCmAmGmGmGmAmCmCmUmAmAmGmAm-CmAmCmAmUmGmUmCmCmC mUmGmGmC-idT (SEQ ID No.: 5) (BT100), where "NH" is a 5'-hexylamine linker phosphoramidite, "idT" is an inverted deoxythymidine, "mN" is a 2'-O-Methyl containing residue.

In some embodiments, the VWF binding agent is an aptamer or a salt thereof comprising the structure: PEG40K-NH-mGmCmCmAmGmGmGmAmCmCmUmAmAmG-mAmCmAmCmAmUmGmUmCmCmC mUmGmGmCidT (SEQ ID No.: 6) (BT200), where "NH" is a 5'-hexylamine linker phosphoramidite, "idT" is an inverted deoxythymidine, "mN" is a 2'-O-Methyl containing residue and "PEG" is a polyethylene glycol and PEG40K is a pegylation moiety having a molecular weight of approximately 40 KDa. It should be understood that the presence of a PEG moiety is optional but when present, may be of varied size.

BT200 (SEQ ID No.: 6) is a PEGylated synthetic RNA oligonucleotide. In addition to PEGylation, BT200 contains a modified phosphorothioate backbone to increase in vivo stability to enable a convenient clinical dosing schedule. BT200 specifically binds to the A1 domain of human VWF, thereby inhibiting the VWF-GPIb interaction, the first step in the cascade of platelet mediated thrombogenesis. The pharmacologic activity of BT200 is shear dependent because the VWF A1 domain is uncoiled and available only under elevated shear force.

BT200 specifically blocks VWF in arterial circulatory systems, and thromboembolism from arterial plaque rupture. Functional inhibition of platelet thrombogenesis by BT200 has been demonstrated by in vitro human pharmacology studies and in vivo studies in nonhuman primates (e.g., as discussed in the PCT Patent Application Publication No.: WO 2018213697; the contents of which are herein incorporated by reference in their entirety). Different from conventional platelet inhibitors of platelet activation (e.g., aspirin, clopidogrel, ticagrelor) and of platelet aggregation (e.g., abciximab, tirofiban), BT200 acts at the upstream step in the cascade of platelet thrombogenesis. In some examples, BT200 can be used as complementary drugs to these conventional anti-platelet drugs.

In some embodiments, the VWF binding agent is a polynucleotide with a fatty acid conjugate, wherein the polynucleotide comprises the sequence selected from SEQ ID No.: 3, (5'GCCAGGGACCUAAGACACAUGUCC-CUGGC-3'), SEQ ID No.: 4 (5' mGmCmCmAmGmGmG-mAmCmCmUmAmAmGmAmCmAmCmAmUmG-mUmCmCmC mUmGmGmC-idT3'), and SEQ ID No.: 5 (5' NH2-mGmCmCmAmGmGmGmAmCmCmUmAmAmG-mAmCmAmCmAmUmGmUmCmCmC mUmGmGmC-idT3'). In one embodiment, the fatty acid may be conjugated to a synthetic polynucleotide comprising at least 21 contiguous nucleotides of SEQ ID No.: 3. In some embodiments, the fatty acid may be conjugated to a synthetic polynucleotide having at least 50%, 55%, 60%, 65%, 70%, 75%, 80%, 90%, 95%, 96%, 97%, 98%, 99% or 100% sequence identity to SEQ ID No.: 3.

In some embodiments, the fatty acid conjugated VWF binding agents can bind to VWF and interfere the activity of VWF.

In some embodiments, the fatty acid conjugated VWF binding agents can be used for secondary stroke prevention and adjunct to carotid angioplasty/stenting as targeted therapeutic indications.

In other embodiments, the VWF binding agent may comprise the sequence PEG40K-NH-mGmGmGmAm-CmCmUmAmAmGmAmCmAmCmAmUmG-mUmCmCmC-idT (ARC15105) (SEQ ID No.: 7) or PEG20K-NH-mGmCmGmUdGdCdAmGmUmGmCmC-mUmUmCmGmGmCdCmGsdTmGdCdGdGdTm GmCdCmUdCdCmGmUdCmAmCmGmCidT (ARC1779) (SEQ ID No.: 8), where "NH" is a 5'-hexylamine linker phosphoramidite, "idT" is an inverted deoxythymidine, "mN" is a 2'-O-Methyl containing residue, "dN" is a deoxynucleotide residue, "sdT" is a phosphorothioate deoxythymidine residue and "PEG" is a polyethylene glycol and PEG20K is a pegylation moiety having a molecular weight of approximately 20 Kda.

In some embodiments, the VWF binding agent may include a synthetic polynucleotide having at least 50%, 55%, 60%, 65%, 70%, 75%, 80%, 90%, 95%, 96%, 97%, 98%, 99% or 100% sequence identity to SEQ ID No.: 7.

In other embodiments, the VWF binding agent is a synthetic polynucleotide comprising the sequence of SEQ ID NO.: 7 with a fatty acid conjugate.

Other aptamers that bind to and inhibit VWF mediated platelet adhesion and arterial thrombosis include but are not limited to, DTRI-031 disclosed by Nimjee et al (Preclinical development of a vWF aptamer to limit thrombosis and engender arterial recanalization of occluded vessels, *Mol. Ther.,* 2019; 27 (7): 1228-1241); Ds-containing DNA aptamers targeting VWF A1-domain disclosed by Matsunaga et al (High-Affinity DNA Aptamer Generation Targeting von Willebrand Factor A1-Domain by Genetic Alphabet Expansion for Systematic Evolution of Ligands by Exponential Enrichment Using Two Types of Libraries Composed of Five Different Bases, *J Am. Chem. Soc.,* 2017; 139 (1): 324-334); the contents of each of which are incorporated by reference in their entirety. Other anti-VWF aptamers include those disclosed in the PCT patent application publication No.: WO2018053427; the contents of which are incorporated herein by reference in their entirety.

The present VWF binding agents can be used for secondary stroke prevention and adjunct to carotid angioplasty/stenting as targeted therapeutic indications. While these patient populations are expected to benefit from the inhibition of thrombogenesis by the VWF binding agents, in emergency situations such as life-threatening major bleeding or non-elective major surgery, reversal strategies should be established (Christos and Naples, Anticoagulation reversal and treatment strategies in major bleeding: Update 2016. *West J Emerg Med.* 2016; 17 (3): 264-270).

To compromise the side effect of bleeding, reversal agents of VWF binding agents may be used in combination with these VWF binding agents to modulate VWF activities. For example, one or more antidotes of an anti-VWF aptamer may be used in combination with the corresponding anti-VWF aptamer to modulate VWF activities. Use of aptamer-antidote pairs could allow for fine-tuning of agent bioavailability and greatly reduce adverse effects and expand the clinical use of these agents.

Reversal Agents of Anti-VWF Aptamers

Aptamers are synthetic oligonucleotides, which can be the code for their own complement (antidote) that can be developed and used to inhibit their function (e.g., Vavalle et al., The REGI anticoagulation system: a novel actively controlled factor IX inhibitor using RNA aptamer technology for treatment of acute coronary syndrome. *Future Cardiol.* 2012; 8 (3): 371-382). The complementary antidote to an aptamer can reverse aptamer induced activities and is also referred to as "reversal agent." In some embodiments, the antidote maybe a universal antidote.

As used herein, the term "reversal agent" refers to an agent that alters, mitigates, neutralizes or reverses the effect of its target agent. A reversal agent of the present disclosure may be the complementary nucleic acid to an aptamer and reverse the activity of such aptamer. For example, a reversal agent may reverse and neutralize between the interaction between a binding agent and its target. "Neutralizing" the aptamer refers to decreasing either the anti-thrombotic or thrombolytic activity of the aptamer.

In some embodiments, reversal agents are competitive binding molecules. In some embodiments, reversal agents bind to VWF binding agents. In some embodiments, reversal agents are nucleic acid molecules, e.g., complementary synthetic polynucleotides which are capable of hybridizing with, and/or binding to, the whole or any part of a VWF binding agent. In the case of nucleic acid based VWF binding agents such as aptamers, reversal agents may hybridize with all, a portion, a region of a VWF binding aptamer. Reversal agents may comprise any, or all of the modifications described herein. In some embodiments, a reversal agent may be a complementary oligonucleotide antidote or a universal antidote. As non-limiting examples, the reversal agent is a complementary antidote that is about 10-40 nucleotides, or 10-30 nucleotides, or 15-30 nucleotides in length. The reversal agent is 15, 16, 17, 18, 19, 20, 21, 22, 23, 24, 25, 26, 27, 28, 29 or 30 nucleotides in length.

In some embodiments, a reversal agent may comprise 10-30 nucleotides, e.g., at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides complementary to the sequence of a VWF binding agent . . . . The reverse agent may be about 70%, 75%, 80%, 85%, 90%, 91%, 92%, 93%, 94%, 95%, 96%, 97%, 98%, 99%, or 100% complementary to the VWF binding agent.

In some embodiments, the reversal agent is chemically modified. Potential modifications include, but are not limited to, for example, (a) end modifications, e.g., 5' end modifications (phosphorylation, dephosphorylation, conjugation, inverted linkages, etc.), 3' end modifications (conjugation, DNA nucleotides, inverted linkages, etc.), (b) sugar modifications (e.g., at the 2' position or 4' position) or replacement of the sugar, (c) base modifications, e.g., replacement with modified bases, stabilizing bases, destabilizing bases, or bases that base pair with an expanded repertoire of partners, or conjugated bases, as well as (d) internucleoside linkage modifications, including modification or replacement of the phosphodiester linkages.

In some embodiments, the chemical modification is selected from a chemical substitution of the nucleic acid at a sugar position, a chemical substitution at a phosphate position and a chemical substitution at a base position. In other embodiments, the chemical modification is selected from incorporation of a modified nucleotide; 3' capping; 5' capping; conjugation to a high molecular weight, non-immunogenic compound; conjugation to a lipophilic compound, such as a fatty acid; and incorporation of phosphorothioate into the phosphate backbone.

In some embodiments, modifications to the sugar may consist of a 2' O-methyl modification. In some embodiments, terminal cap structures may also be incorporated to the 3' and/or 5' termini. Such structures include, but are not limited to, at least one inverted deoxythymidine or amino group (NH2). In one embodiment, the 3' cap is an inverted deoxythymidine cap. In another embodiment, the 3' cap is an amino group (NH2). In one embodiment, the 5' cap is an inverted deoxythymidine cap. In another embodiment, the 5' cap is an amino group (NH2).

In some embodiments, the reversal agent may also be modified by conjugation to a moiety having desired biological properties. In some embodiments, the reversal agents described herein may comprise conjugates, including but not limited to, a protein, an antibody or variant thereof, a carbohydrate, a peptide, a lipid, a lipophilic compound such as a fatty acid, a polymer, and a small molecule.

In some embodiments, the reversal agent is conjugated with a polymer such as a polyethylene glycol (PEG) polymer or derivatives thereof. In other embodiments, the reversal agent is conjugated with a fatty acid moiety.

In some embodiments, the reversal agent and the VWF binding agent may comprise the same conjugate moiety. In other embodiments, the reversal agent and the VWF binding agent may comprise different conjugate moieties.

In some embodiments, the activity of the VWF binding agent may be reversed by the reversal agents. In some embodiments, the activity of the VWF binding agent may be reversed by about 20 to 100%, or about 30 to 100%, or about 40 to 100%, or about 50 to 100%, or about 60 to 100%, or about 70 to 100%, or about 80 to 100%, or about 90 to 100%, or about 50%, or about 55%, or about 60%, or about 65%, or about 70%, or about 75%, or about 80%, or about 85%, or about 90%, or about 95%, or about 100%.

In some examples, a reversal agent comprises a nucleic acid sequence complementary to the VWF binding agent BT200 (SEQ ID No.: 6). The reverse agent may comprise a nucleic acid sequence that is about 70%, 75%, 80%, 85%, 90%, 91%, 92%, 93%, 94%, 95%, 96%, 97%, 98%, 99%, or 100% complementary to the sequence of BT200 (SEQ ID NO.: 6). As non-limiting examples, the reversal agent is a synthetic oligonucleotide comprising the nucleic acid sequence presented by 5'-ACAUGUGUCUUAGGUCC-CUGGC-3' (SEQ ID No.: 9). In some embodiments, the reversal agent comprises at least 10, 11, 12, 13, 14, 15, 16, 17, 18, 19, 20 or 21 contiguous nucleotides of SEQ ID No.: 9. In other embodiments, the reversal agent may comprise a synthetic polynucleotide having at least 50%, 55%, 60%, 65%, 70%, 75%, 80%, 90%, 91%, 92%, 93%, 94%, 95%, 96%, 97%, 98%, 99% or 100% sequence identity to SEQ ID No.: 9.

In another embodiment, the reversal agent comprises the nucleic acid sequence 5'mAmCmAmUmGmUmGmUmC-mUmUmAmGmGmUmCmCmCmUmGmGmC-idT 3' (SEQ ID No.: 10) (BT101) (BT101 is also referred to as BT201 in Applicant's PCT Patent Application Publication No.: WO 2018213697), where "idT" is an inverted deoxythymidine at the 3'teminus of the sequence, "mN" is a 2'-O-Methyl containing residue.

The nucleic acid sequence of the reversal agent BT101 and base pairing with BT200 are shown in FIG. 1B. BT101 can directly interact with the core aptamer of BT200, impacting the interaction of BT200 with human VWF. The binding between BT101 and BT200 can reverse BT200 induced inhibition of platelet function (e.g., thrombus formation).

In some examples, the activity of the VWF binding agent may be reversed using the reversal agent of the present disclosure by about 10 to 100%, or about 20 to 100%, or about 30 to 100%, or about 40 to 100%, or about 50 to 100%, or about 60 to 100%, or about 70 to 100%, or about 80 to 100%, for example, about 50%, or about 60%, or about 70%, or about 80%, or about 90%, or about 95%, or about 100%.

In some embodiments, BT101 contains an unmodified phosphate backbone in order to limit its stability in the systemic circulation and enable fine control of reversal activity.

In some embodiments, the reversal agent BT101 may be used to reverse BT200 in a condition that a subject under treatment with BT200 needs a medical procedure, e.g., having an accident.

TABLE 1

VWF aptamers and reversal agents

| Agent | Sequence (5'-3') and modifications | SEQ ID NO |
|---|---|---|
| VWF aptamer | GCCAGGGACCUAAGACACAUGUCCCUGGC | 3 |
| BT99 | mGmCmCmAmGmGmGmAmCmCmUmAmAmGmAmCmAm CmAmUmGmUmCmCmCmUmGmGmC-idT | 4 |
| BT100 | $NH_2$-mGmCmCmAmGmGmGmAmCmCmUmAmAmGmAm CmAmCmAmUmGmUmCmCmCmUmGmGmC-idT | 5 |
| BT200 | PEG40K-NH- mGmCmCmAmGmGmGmAmCmCmUmAmAmGmAmCmAm CmAmUmGmUmCmCmCmUmGmGmC-idT | 6 |
| Reversal sequence | ACAUGUGUCUUAGGUCCCUGGC | 9 |
| BT101 | mAmCmAmUmGmUmGmUmCmUmUmAmGmGmUmCmCm CmUmGmGmC-idT | 10 |

In some embodiments, reversal agents of VWF binding agents may be used in combination with these conjugated VWF binding agents to modulate VWF activities. For example, one or more antidotes of an anti-VWF aptamer may be used in combination with the corresponding anti-VWF aptamer to modulate VWF activities. Use of aptamer-antidote pairs could allow for fine-tuning of agent bioavailability and greatly reduce adverse effects and expand the clinical use of these agents.

Pharmaceutical Compositions

In another aspect of the present disclosure, pharmaceutical compositions and formulations including any one of anti-VWF aptamers and their reversal agents of the present disclosure are provided. The compositions further include at least one pharmaceutically acceptable carrier, diluent or excipient. The composition may be formulated for administration by parental administration or enteral administration, or other appropriate routes. Parental administration may be performed by injection, or by the insertion of an indwelling catheter, including but not limited to intravenous (IV), intramuscular (IM), subcutaneous (SC), percutaneous injection, peridural injection, intracerebral (into the cerebrum) administration, intracerebroventricular (into the cerebral ventricles) administration, extra-amniotic administration, nasal administration, intra-arterial, intracardiac, intraosseous infusion (IO), intraperitoneal infusion or injection, transdermal diffusion, enteral and gastrointestinal routes, topical administration and oral routes.

In some embodiments, the VWF binding agent and its reversal agent(s) may be formulated in moles at a ratio from 20:1 to 1:20, or from 10:1 to 1:10, or from 5:1 to 1:5. In one preferred embodiment, the VWF binding agent and its reversal agent is formulated in moles at a ratio of 1:1, or 1:1.5, or 1:2, or 1:3, or 1:4, or 1:5, or 1:10. In some embodiments, the VWF binding agent and its reversal agent(s) are formulated separately, and in other embodiments, the VWF binding agent and its reversal agent(s) are formulated together as complex compositions.

In some embodiments, the composition for regulating VWF activity is composed of a VWF binding agent that binds to VWF and inhibits VWF activity and a reversal agent that neutralizes/reverses the effect of the VWF binding agent. The VWF binding agent is an aptamer or variant thereof and the reversal agent is an antidote, comprising a nucleic acid sequence complementary to the sequence of the VWF binding aptamer.

In some embodiments, the VWF binding agent comprises a nucleic acid sequence of SEQ ID NO.: 3 or variant thereof, and the reversal agent comprises a nucleic acid sequence of SEQ ID NO.: 9 or variant thereof. The VWF binding agent and the reversal agent may include at least one nucleotide modification with 2'-O-methyl modification. In some embodiments, the VWF binding agent is modified with a conjugate selecting from the group consisting of a polymer, a protein, an antibody or variant thereof, a peptide, a lipid, a fatty acid, a carbohydrate, and a small molecule. For example, the VWF binding agent is conjugated with a PEG polymer or a fatty acid. In other embodiments, the reversal agent is also modified with a conjugate selecting from the group consisting of a polymer, a protein, an antibody or variant thereof, a peptide, a lipid, a fatty acid, a carbohydrate, and a small molecule. The VWF binding agent and its reversal agent(s) may include the same conjugate moiety. The VWF binding agent and its reversal agent(s) may include different conjugate moieties.

In some embodiments, the VWF binding agent comprises a nucleic acid sequence selected from the group of SEQ ID Nos.: 4-6 and variants thereof, and the reversal agent comprises a nucleic acid sequence of SEQ ID No.: 10 or variant thereof. As a non-limiting example, the VWF binding agent comprises a nucleic acid sequence presented by SEQ ID No.: 6 (BT200) or variant thereof, and the reversal agent comprises a nucleic acid sequence presented by SEQ ID No.: 10 (BT101) or variant thereof.

Provided in the present disclosure further include kits for therapeutic use comprising a VWF binding agent and a reversal agent as described herein.

In some embodiments, the kit for therapeutic use comprises 1) a VWF binding agent having a sequence selected from the group consisting of SEQ ID Nos.: 3-6 and variants thereof; 2) a reversal agent that reverses the effect of the VWF binding agent and that includes a nucleic acid sequence complementary to the sequence or a portion of the sequence of the VWF binding agent; and 3) an introduction for use of the kit.

In some embodiments, the kit may further comprise an assay part for measuring VWF levels.

In some embodiments, the reversal agent of the kit comprises a nucleic acid sequence selected from the group consisting of SEQ ID Nos: 9 to 10 and variants thereof.

In one preferred embodiment, the kit for therapeutic use includes a VWF binding agent comprising the nucleic acid sequence of SEQ ID No.: 6 (BT200) or variant thereof and a reversal agent comprising the nucleic acid sequence of SEQ ID No.: 10 (BT101) or variant thereof.

Kit components may be packaged in liquid (e.g., aqueous, or organic) media or in dry (e.g., lyophilized) form. Kits may include containers that may include, but are not limited to vials, test tubes, flasks, bottles, syringes, or bags. Kit containers may be used to aliquot, store, preserve, insulate, and/or protect kit components. Kit components may be packaged together or separately. Some kits may include containers of sterile, pharmaceutically acceptable buffer and/or other diluent (e.g., phosphate buffered saline). In some embodiments, kits include containers of kit components in dry form with separate containers of solution for dissolving dried components. In some embodiments, kits include a syringe for administering one or more kit components.

Containers may include at least one vial, test tube, flask, bottle, syringe and/or other receptacle, into which VWF binding agent and reversal agent formulations may be placed, preferably, suitably allocated. Kits may also include containers for sterile, pharmaceutically acceptable buffer and/or another diluent.

Kits may include instructions for employing kit components as well the use of any other reagent not included in the kit. Instructions may include variations that can be implemented.

In some embodiments, kits are prepared for storage at specific temperatures or temperature ranges. Some kits may be prepared for storage at room temperature. Some kits may be prepared for storage between from about 2° C. to about 8° C. Some kits may be prepared for storage at room temperature.

Methods and Applications

Modulation of VWF Function

In one aspect, VWF binding agents and reversal agents of the present disclosure are used together to modulate VWF activity in a blood circulatory system. According to the present disclosure, methods of modulating VWF function in a blood circulatory system comprising introducing to the circulatory system an effective amount of a VWF binding agent that binds to VWF and inhibits the activity of VWF in the blood, and introducing to the circulatory system an effective amount of a reversal agent of the VWF binding agent that sequesters/reverses the effects of the VWF binding agent and that includes a nucleic acid sequence complementary to the sequence or a portion of the sequence of the VWF binding agent, wherein the introduction of the reversal agent is done after administering the VWF binding agent. In some embodiments, the VWF binding agent is an aptamer or variant thereof, which binds to VWF and the reversal agent is a complementary antidote of the VWF binding aptamer.

In some embodiments, the VWF binding agent is a VWF binding aptamer comprising the nucleic acid sequence presented by SEQ ID NO.: 3, or variant thereof. The sequence of the VWF binding aptamer may include at least one nucleotide modification with 2'-O-methyl modification. In other examples, the VWF binding aptamer is further modified with a conjugate, which includes but is not limited to, a polymer, a protein, an antibody or variant thereof, a peptide, a lipid, a fatty acid, a carbohydrate, and a small molecule. For example, the VWF binding agent is conjugated with a PEG polymer or a fatty acid. In some embodiments, the reversal agent comprises the nucleic acid sequence of SEQ ID NO.: 9, or variant thereof. The reversal agent (i.e., the complementary antidote) may include at least one nucleotide modification with 2'-O-methyl modification. In other examples, the reversal agent is further modified with a conjugate, which includes but is not limited to a polymer, a protein, an antibody or variant thereof, a peptide, a lipid, a fatty acid, a carbohydrate, and a small molecule. In some embodiments, the VWF binding aptamer and its reversal agent comprise the same modifications such as a PEG polymer and a fatty acid. In other embodiments, the VWF binding aptamer and its reversal agent comprise different modifications.

In some embodiments, the VWF binding agent comprises a nucleic acid sequence selected from the group consisting of SEQ ID Nos.: 4-6 and variants thereof, and wherein the reversal agent comprises a nucleic acid sequence of SEQ ID No.: 10 or variant thereof.

In one preferred embodiment, the method of modulating VWF activity in a blood circulatory system comprising introducing to the circulatory system an effective amount of a VWF binding agent comprising the nucleic acid sequence presented by SEQ ID No.: 6 (BT200) or variant thereof; and introducing to the circulatory system an effective amount of a reversal agent comprising the nucleic acid sequence presented by SEQ ID No.: 10 (BT101) or variant thereof, wherein the introduction of the reversal agent is done after the administering the VWF binding agent, and wherein the reversal agent sequesters/reverses the effects of the VWF binding agent.

In some embodiments, the amount of the reversal agent is based on the amount of the VWF binding agent previously administered and the ratio of the reversal agent and the binding agent is based on a desired reduction in the activity of the VWF binding agent. In some examples, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some embodiments, the activity of the VWF binding agent is reversed by the reversal agent by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In another aspect, the present disclosure provides methods for modulating VWF activity in a subject comprising administering to the circulatory system of the subject an effective amount of a VWF binding agent having a nucleic acid sequence that binds to and inhibits the activity of VWF, and administering to the circulatory system of the subject an effective amount of a reversal agent that sequesters/reverses the effects of the VWF binding agent and that includes a nucleic acid sequence complementary to the sequence or a portion of the sequence of the VWF binding agent. The introduction of the reversal agent is done after the administering the VWF binding agent.

In some embodiments, the method of modulating VWF activity in a subject comprises the steps of 1) administering to the subject an effective amount of a VWF binding agent comprising a nucleic acid sequence selecting from the group consisting of SEQ ID Nos.: 3-6 and variants thereof, and 2) administering to the subject an effective amount of a reversal agent comprising a nucleic acid sequence selected from the group consisting of SEQ ID Nos.: 9-10 or variants thereof, wherein the introduction of the reversal agent is done after the administering the VWF binding agent, and wherein the reversal agent sequesters/reverses the effects of the VWF binding agent.

In this context, the VWF binding agent inhibits the VWF-platelet interaction and the VWF-erythrocyte interaction, thereby inhibiting platelet mediated thrombosis in the circulatory system. The VWF binding agent may interfere the interaction between VWF and Factor VIII. The reversal agent reverses the inhibitory effects induced by the VWF binding agent. The reversal agent restores the VWF-platelet interaction and the VWF-erythrocyte interaction. The reversal agent may relieve the interfering effect on the VWF-Factor VIII interaction.

In one preferred embodiment, the method for modulating VWF activity in a subject includes use of the VWF binding agent comprising the nucleic acid sequence of SEQ ID No.: 6 (BT200) or variant thereof, and the reversal agent comprising the nucleic acid sequence of SEQ ID No.: 10 (BT101) or variant thereof. BT200 inhibits the VWF-platelet interaction and the VWF-erythrocyte interaction. BT101 reverses the inhibition induced by BT200.

The amount of the reversal agent is based on the amount of the VWF binding agent previously administered and the ratio of the reversal agent and the binding agent is based on a desired reduction in the activity of the VWF binding agent. In some examples, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some examples, the activity of the VWF binding agent may be reversed by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In some embodiment, the reversal agent is administered at about 24 hours, or 36 hours, or 48 hours, or 60 hours, or 72 hours, or four days, or a week after administration of the VWF binding agent.

Prevention of Thrombosis and Thrombolytic Treatment

VWF binding agents and reversal agents of the present disclosure are used to prevent thrombus formation and/or treat a thrombotic disorder in a patent in need. In some embodiments, the VWF binding agents may be used as anti-thrombotic drugs to prevent formation of blood clots. In other embodiments, the VWF binding agents may be used as thrombolytic drugs to dissolve thrombi in a circulatory system. The reversal agents may be used, together with the VWF binding agents to reverse the inhibitory effects induced by the VWF binding agents. Accordingly, methods for preventing thrombus formation and/or treating a thrombotic disorder in a patient in need comprise administering to the patient a therapeutically effective amount of any one of the agents and compositions described herein.

In one aspect, the present disclosure provides methods of preventing, or preventing the progression of, or alleviating, thrombosis in a patient.

In some embodiments, the method of preventing, or preventing the progression of, or alleviating, thrombosis (i.e., thrombus formation) associated with a clinical condition in a patient in need comprises the steps of 1) administering to the patient a therapeutically effective amount of a VWF binding agent comprising a nucleic acid sequence that binds to VWF and inhibits the activity of VWF; and 2) administering to the patient a therapeutically effective amount of a reversal agent that sequesters/reverses the effects of the VWF binding agent and that comprises a second nucleic acid sequence complementary to the sequence or a portion of the sequence of the VWF binding agent. Optionally, a step for measuring the VWF level in the blood of the patient may be performed before administering the reversal agent to the patient. The reversal agent is administered when the patient receiving the treatment of the VWF binding agent and compositions thereof is under the threat of hemorrhage.

In some embodiments, the VWF binding agent is an aptamer, or variant thereof, which binds to VWF and inhibits VWF activity. The reversal agent is a complementary antidote of the VWF binding aptamer. In one embodiment, the VWF binding agent is a VWF binding aptamer comprising the nucleic acid sequence presented by SEQ ID NO.: 3, or variant thereof. In some examples, the sequence of the VWF binding aptamer may include at least one nucleotide modification with 2'-O-methyl modification. In other examples, the VWF binding aptamer is further modified with a conjugate, which includes but is not limited to a polymer, a protein, an antibody or variant thereof, a peptide, a lipid, a fatty acid, a carbohydrate, and a small molecule. For example, the VWF binding agent may be conjugated with a PEG polymer or a fatty acid.

In one embodiment, the reversal agent comprises the nucleic acid sequence presented by SEQ ID NO.: 9, or variant thereof. The reversal agent may include at least one nucleotide modification with 2'-O-methyl modification. In other examples, the reversal agent is further modified with a conjugate, which includes but is not limited to a polymer, a protein, an antibody or variant thereof, a peptide, a lipid, a fatty acid, a carbohydrate, and a small molecule. In some embodiments, the VWF binding aptamer and its reversal agent comprise the same modifications such as a PEG polymer and a fatty acid. In other embodiments, the VWF binding aptamer and its reversal agent comprise different modifications.

In some embodiments, the VWF binding agent comprises a nucleic acid sequence selected from the group consisting of SEQ ID Nos.: 4-6 and variants thereof, and the reversal agent comprises a nucleic acid sequence of SEQ ID No.: 10 or variant thereof.

In some embodiments, the method of preventing, or preventing the progression of, or alleviating, thrombosis in the patient comprises the steps of 1) administering to the patient a therapeutically effective amount of a VWF binding agent comprising the sequence of SEQ ID NO.: 3, or variant thereof, and 2) administering to the patient a therapeutically effective amount of an effective amount of a reversal agent having a sequence complementary to the sequence of the VWF binding agent, wherein the reversal agent sequesters/reverses the effects of the VWF binding agent. In some aspects, the reversal agent comprises the sequence of SEQ ID NO.: 9, or variant thereof.

In one preferred embodiment, the method of preventing, or preventing the progression of, or alleviating, thrombosis associated with a clinical condition in a patient uses the VWF binding agent comprising the nucleic acid sequence of SEQ ID No.: 6 (BT200) or variant thereof and the reversal agent comprising the nucleic acid sequence of SEQ ID No.: 10 (BT101) or variant thereof.

The amount of the reversal agent is based on the amount of the VWF binding agent previously administered and the ratio of the reversal agent and the binding agent is based on a desired reduction in the activity of the VWF binding agent. In some embodiments, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some examples, the activity of the VWF binding agent may be reversed by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In some embodiments, the reversal agent is administered when the patient under the treatment with the VWF binding agent and compositions thereof at risk of bleeding.

The patient in need of prevention of thrombus formation may need prevention of thrombi associated with, for example without limitation, stroke (e.g., ischemic stroke, transient ischemic attack (TIA), silent ischemia), cerebrovascular thrombi, deep vein thrombosis (DVT), pulmonary embolism (PE), femoral vein thrombosis, myocardial infarction (heart attack), atrial fibrillation, coronary artery thrombus, superior vena-cava thrombosis, jugular vein thrombosis, cerebral venous sinus thrombosis, retinal vein occlusion, intra-cardiac thrombi, post-surgical thrombi, cancer-induced thrombosis, cancer-related thrombin expression, infection, disseminated intravascular coagulation (DIC), and arterial thrombosis including cerebral arteries, coronary arteries and peripheral arteries in the head and neck, visceral arteries, arms and legs arteries.

The patient in need of treatment or prevention of thrombi may be in need for treatment and prevention of primary ischemic stroke, secondary ischemic stroke, cerebrovascular thrombi, arterial thrombi, PE, atrial fibrillation, large artery atherosclerosis (LAA) (extracranial and intracranial disease), small artery occlusion (lacunar), cryptogenic stroke, ICAS, cardioembolism, post-surgical thrombotic complications, and thrombi induced by infection and cancer, etc.

In some embodiments, the VWF levels may be predetermined in patients to identify the population suitable for treatment with the VWF binding agents. In accordance with the present invention, the method further comprises monitoring/measuring the VWF levels before and post treatment with the present VWF agents and compositions. In other embodiments, the patient is diagnosed with VWF-rich blood clots. The VWF-rich thrombi may be identified by computed tomography or magnetic resonance imaging (MRI). This evaluation will assist in developing an approach for individualized stroke therapy. Plasma VWF antigen and plasma VWF activity can be assayed using methods well-known in the art. Plasma VWF antigen may be identified by ELISA on microtiter plates with antibodies to VWF. VWF activity is commonly assayed for example as ristocetin cofactor activity.

In some embodiments, patients at high risk of certain sub-types of stroke may be treated with the present compositions and methods. The patients comprise a subpopulation of patients that are prone to developing VWF-mediated stroke, such as ischemic stroke, including subtypes of large artery atherosclerosis (LAA) (extracranial and intracranial disease), small artery occlusion (lacunar), cardioembolism and other determined or undetermined etiologies.

In further another aspect of the present disclosure, VWF agents and methods described herein are of use for preventing thrombus formation and/or treating a thrombotic disorder in a patient in need. The method for preventing thrombus formation and/or treating a thrombotic disorder in the patient comprises administering to the patient a therapeutically effective amount of a VWF binding agent. The VWF binding agent is aptamer that binds to VWF and inhibits VWF activity, or variant thereof.

In some embodiments, the VWF binding agent comprises a nucleic acid sequence of SEQ ID No.: 3 or variant thereof. The VWF binding aptamer may include at least one nucleotide modification with 2'-O-methyl modification. The VWF binding aptamer may be further modified with a conjugate, which includes but is not limited to a polymer, a protein, an antibody or variant thereof, a peptide, a lipid, a fatty acid, a carbohydrate, and a small molecule. In some examples, the VWF binding agent comprises a sequence selected from the group consisting of SEQ ID Nos. 4-6 and variants thereof. As a non-limiting example, the VWF binding agent comprises the nucleic acid sequence of SEQ ID No.: 6 (BT200) or variant thereof.

In some embodiments, a reversal agent and a composition thereof may be administered to the patient under the treatment with a VWF binding agent in a situation that the patient is at risk of hemorrhagic bleeding. The reversal agent rapidly reverses the inhibitory effect induced by the VWF binding agent. In some embodiments, the reversal agent is a complementary antidote of the VWF binding aptamer. For example, the reversal agent may comprise a synthetic polynucleotide that is complementary to the sequence or a portion of the sequence of the VWF binding agent that includes the sequence of SEQ ID No.: 3. In some examples, the reversal agent comprises the nucleic acid sequence of SEQ ID No.: 9 or variant thereof. The reversal agent may include at least one nucleotide modification with 2'-O-methyl modification. The reversal agent may be further modified with a conjugate, which includes but is not limited to a polymer, a protein, an antibody or variant thereof, a peptide, a lipid, a fatty acid, a carbohydrate, and a small molecule. As a non-limiting example, the reversal agent comprises the nucleic acid sequence of SEQ ID No.: 10 (BT101) or variant thereof.

In further another aspect, the present disclosure provides method of treating, preventing, or preventing the progression of, or alleviating, a clinical condition associated with elevated levels of VWF in a subject comprising administrating to the subject an effective amount of a VWF binding agent comprising a nucleic acid sequence that binds to VWF and inhibits VWF activity; and administering to the subject an effective amount of a reversal agent that reverses/neutralizes the effect of the treatment agent and that comprises a second nucleic acid sequence complementary to the sequence or a portion of the sequence of the VWF binding agent. The reversal agent is administered when the levels of plasma VWF need to be increased in the patient receiving the treatment of the VWF binding agent and composition thereof.

In some embodiments, the VWF binding agent is a VWF aptamer and the reversal agent is a complementary antidote of the VWF binding aptamer. In some embodiments, the VWF binding agent comprising the sequence of SEQ ID NO.: 3, or variant thereof. The VWF binding aptamer may include at least one nucleotide modification with 2'-O-methyl modification. The VWF binding aptamer may be further modified with a conjugate, which includes but is not limited to a polymer, a protein, an antibody or variant thereof, a peptide, a lipid, a fatty acid, a carbohydrate, and a small molecule.

Similarly, the reversal agent may include at least one nucleotide modification with 2'-O-methyl modification. The reversal agent may be further modified with a conjugate, which includes a polymer, a protein, an antibody or variant thereof, a peptide, a lipid, a fatty acid, a carbohydrate, and a small molecule.

In some examples, the VWF binding agent comprises a nucleic acid sequence selected from the group consisting of SEQ ID Nos.: 4-6 and variants thereof. As a non-limiting example, the VWF binding agent comprises the nucleic acid sequence of SEQ ID No.: 6 (BT200) or variant thereof.

In some embodiments, the reversal agent comprises the nucleic acid sequence of SEQ ID NO.: 9, or variant thereof. The reversal agent may include at least one nucleotide modification with 2'-O-methyl modification. The reversal agent may be further modified with a conjugate, which includes but is not limited to a polymer, a protein, an antibody or variant thereof, a peptide, a lipid, a fatty acid, a carbohydrate, and a small molecule. As a non-limiting example, the reversal agent comprises the nucleic acid sequence of SEQ ID No.: 10 (BT101) or variant thereof.

In one preferred embodiment, the method of treating, preventing, or preventing the progression of, or alleviating, a clinical condition associated with elevated levels of VWF in a subject is of use of the VWF binding agent having the sequence of SEQ ID No.: 6 (BT200) or variant thereof, and the reversal agent having the sequence of SEQ ID No.: 10 (BT101) or variant thereof.

The VWF binding agent inhibits the VWF-Factor VIII interaction, the VWF-platelet interaction and/or the VWF-erythrocyte interaction. The reversal agent reverses the inhibition induced by the VWF binding agent.

The clinical conditions associated with elevated VWF may include but are not limited to ischemic stroke such as primary stroke and secondary stroke, transient ischemic attack (TIA), silent ischemia, cerebrovascular thrombi, arterial thrombi, occlusive thrombi, acute coronary syndrome, and acute occlusion thrombosis.

The amount of the reversal agent is based on the amount of the VWF binding agent previously administered and the ratio of the reversal agent and the binding agent is based on a desired reduction in the activity of the VWF binding agent. In some embodiments, the ratio of the reversal agent and the binding agent is from about 20:1 to 1:20 in moles, or about 10:1 to 1:10 in moles, or about 5:1 to 1:5 in moles. As non-limiting examples, the ratio of the reversal agent and the binding agent is at about 1:1 in moles, or at about 1:1.5 in moles, or at about 1:2 in moles, or at about 1:3 in moles, or at about 1:4 in moles, or at about 1:5 in moles.

In some examples, the activity of the VWF binding agent may be reversed by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

In further another aspect, the present disclosure provides methods of reversing the antithrombotic effect of an agent that binds to and inhibits VWF activity in a subject in need, comprising administering to the subject a reversal agent in amount sufficient to effect said reversal. For example, the agent is a VWF aptamer comprising the sequence of SEQ ID No.: 6 (BT200) and its reversal agent is an antidote of the VWF aptamer, i.e., a synthetic oligonucleotide of SEQ ID No.: 10 (BT101).

In some examples, the activity of the VWF binding agent may be reversed by about 20 to 100%, or about 30 to 100%, or about 40 to 100%, or about 50 to 100%, or about 60 to 100%, or about 70 to 100%, or about 80 to 100%, or about 50%, or about 55%, or about 60%, or about 65%, or about 70%, or about 75%, or about 80%, or about 85%, or about 90%, or about 95%, or about 100%.

The reversal can reduce the adverse effect of bleeding complications caused by anti-thrombotic agents (e.g., anti-VWF aptamers).

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

A number of possible alternative features are introduced during the course of this description. It is to be understood that, according to the knowledge and judgment of persons skilled in the art, such alternative features may be substituted in various combinations to arrive at different embodiments of the present disclosure.

Any patent, publication, internet site, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

EXAMPLES

The present disclosure is further illustrated by the following non-limiting examples.

Example 1: BT101 and BT100 Binding Assay (In Vitro)

The binding of BT101 to the core aptamer of BT200, a non-PEGylated version known as BT100, was evaluated using polyacrylamide gel electrophoresis (PAGE). BT100 and BT101 were each dissolved in 0.9% sodium chloride (physiological saline) at a range of concentrations to enable the mixing of the two compounds at different molar ratios. BT100:BT101 molar ratios tested were 0:1, 1:0, 1:2:1:1, 2:1, and 5:1. Following mixing, the solutions were incubated at 37° C. for 30 minutes prior to loading onto a 20 mL 16% PAGE-urea gel composed of 8 mL 40% acrylamide, 4 mL deionized water, 8 mL 5×TBE (tris base, boric acid, EDTA), 150 μL 10% ammonium persulfate, and 15 μL tetramethylethylenediamine. After gel electrophoresis, the mix was visualized using Bio-Rad Gel Doc XR.

Figure 2:
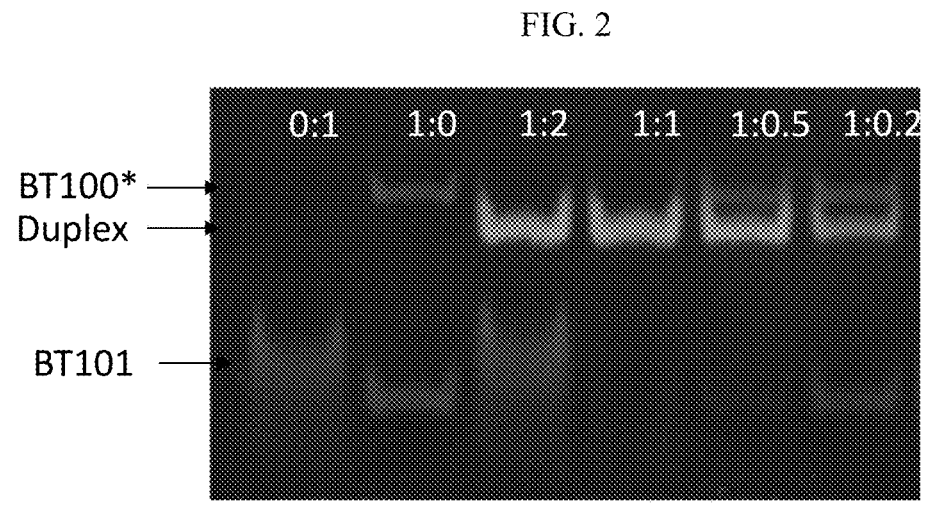

BT-101 bound to BT100 (non-PEGylated version of BT200) in vitro as evidenced by the formation of a duplex that was not see under conditions where BT-100 or BT-101 were loaded directly onto the gel without mixing them together (FIG. 2). Under conditions where BT100 and BT101 were incubated at a 1:1 ratio in moles, only the duplex band was apparent demonstrating nearly complete antidote-aptamer binding. No further formation of duplex was seen under conditions where excess BT100 or excess BT101 was present supporting that the interaction between the two molecules is a 1:1 interaction.

Example 2: Effect of BT101 on the Binding of BT200 to Purified Human VWF

The affinity of BT200, with or without pre-incubation with BT101, for purified human VWF was evaluated using an enzyme-linked immunosorbent assay (ELISA) method. In this study, purified human VWF protein was dissolved in Dulbecco's phosphate buffered saline (dPBS) buffer at a concentration of 10 μg/mL and 100 μL of this solution was added to each well of a Nunc Maxisorp 96-well plate. The plate was incubated overnight at 4° C. The following day, the plate was washed 3 times, followed by blocking with 5% bovine serum albumin (BSA) in dPBS at room temperature for 90 minutes. The blocked plate was then washed 3 times before adding either BT200 at concentrations of 0.3, 1, 3, 10, 30, 100, 300, 1000, 3000, and 10000 nM or a pre-incubated 1:1 molar ratio of BT101:BT200 at the same concentrations. BT101 and BT200 were mixed and incubated at 37° C. for 30 minutes prior to addition to the plate.

Plates were then incubated at 37° C. for 2 hours. Each plate was then washed 3 times and 100 μL of anti-PEG antibody at 1 μg/mL in 1% BSA/dPBS was added to each well and incubated for 1 hour at room temperature. Following an additional 3 washes, 100 μL of anti-rabbit horseradish peroxidase (HRP) in dPBS with 1% BSA was added to each well for 60 minutes at room temperature. To detect HRP, 100 μL of Slow TMB solution was added to each well and incubated at room temperature for 30 minutes. To stop the reaction, 100 μL of 2 N $H_2SO_4$ was added to each well and the plate was then read at 450 nm for absorbance and the mean absorbance under each set of conditions was recorded.

Figure 3:
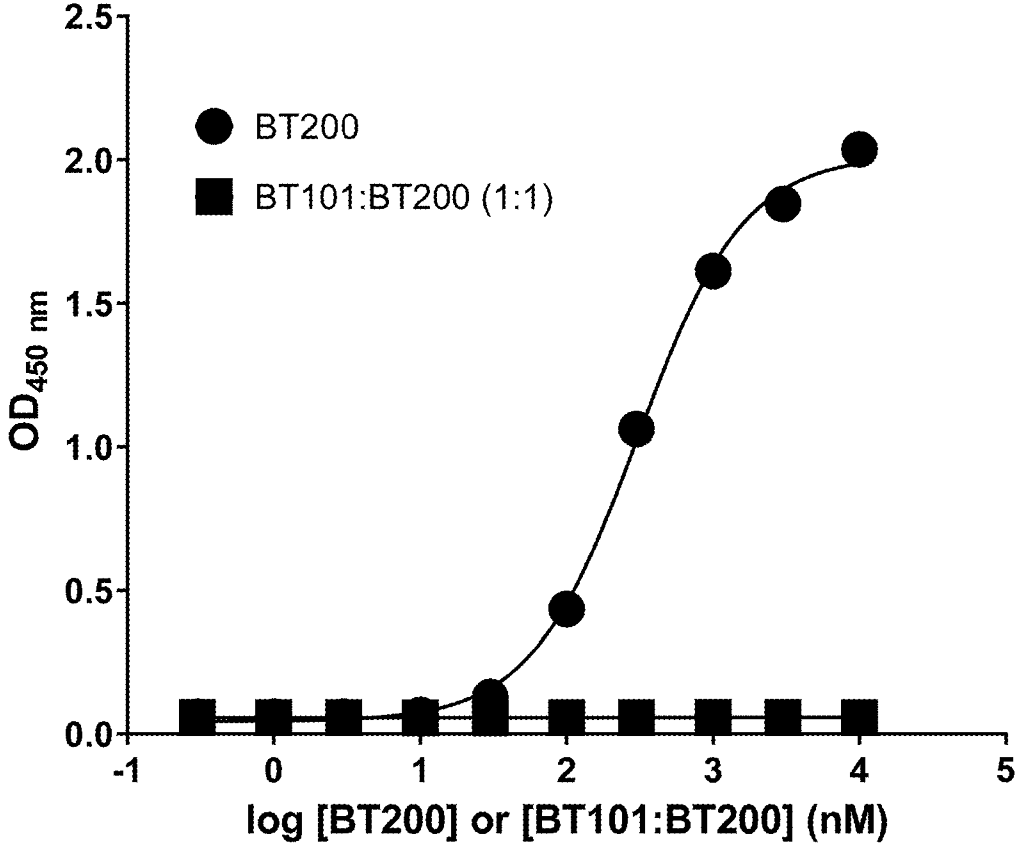
FIG. 3 shows the binding of BT200 to purified human VWF in the absence or presence of a 1:1 molar ratio of BT101 as measured by ELISA.

BT200 bound to purified human VWF in a concentration-dependent manner (FIG. 3). The $EC_{50}$ for the interaction between BT200 and human VWF was 331 nM. Pre-incubation of BT200 with a 1:1 molar ratio of BT101 resulted in complete inhibition of the interaction between BT200 and VWF as no increase in optical density was noted at BT200 concentrations up to 10 μM under these conditions.

Example 3: Effect of BT101 on BT200 Induced Inhibition of VWF Activity

BT-200 was incubated with citrated human plasma at a final concentration of 3 μg/mL for 60 minutes at 37° C. Subsequently, BT101 was added to the incubation at molar ratios of 0:1, 0.5:1, 1:1, and 2:1 and incubated with the plasma containing BT200 for an additional 30 minutes at 37° C. After completion of the incubation period, VWF activity was measured using the REAADS® VWF:Act assay.

The REAADS® VWF:Act assay is a sandwich enzyme-linked immunosorbent assay (ELISA) for VWF activity. Analysis of VWF:Act was performed according to manufacturer's instructions. Briefly, a monoclonal capture antibody specific for the portion of VWF which binds platelets is coated onto 96-microwell polystyrene plates (Goodall et al., An immunoradiometric assay for human factor VIII/Von Willebrand Factor (VIII: VWF) using a monoclonal antibody that defines a functional epitope. *Br J Haematol,* 1985, 59:565-577; and Murdock et al., Von Willebrand factor activity detected in a monoclonal antibody-based ELISA: an alternative to the Ristocetin cofactor platelet agglutination assay for diagnostic use. *Thrombosis and Haemostasis,* 1997, 78 (4): 1272-1277). Diluted plasma is incubated in the wells, allowing any available antigen to bind to the monoclonal antibody on the microwell surface. The plates are washed to remove unbound proteins and other plasma molecules. Bound antigen is quantitated using horseradish peroxidase (HRP) conjugated anti-human VWF detection antibody. Following incubation, unbound conjugate is removed by washing. A chromogenic substrate of tetramethylbenzidine (TMB) and hydrogen peroxide ($H_2O_2$) is added to develop a colored reaction. The intensity of the color is measured in optical density (O.D.) units with a spectrophotometer at 450 nm. VWF:Act in relative percent concentration is determined against a curve made from the reference plasma provided with the kit.

Figure 4:
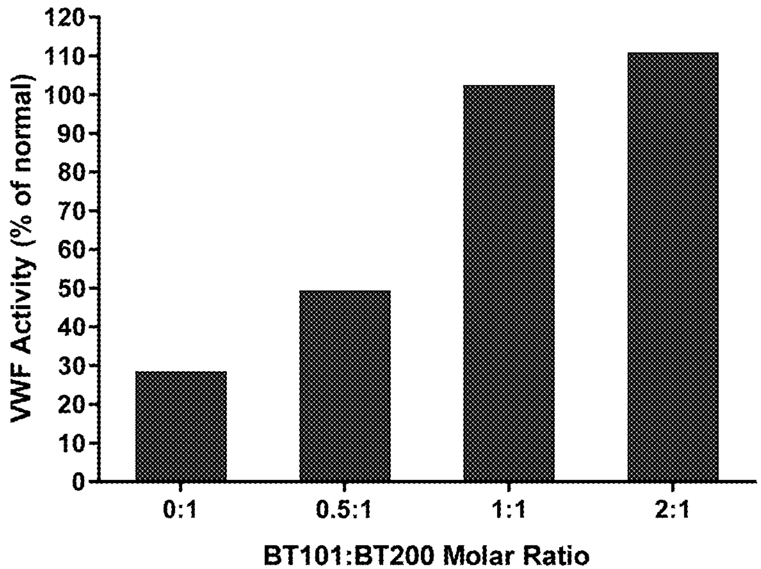
FIG. 4 demonstrates the effects of BT101 on BT200-induced inhibition of VWF activity measured using the REAADS® VWF:Act assay. BT200 was tested at a final concentration of 3 μg/mL with or without different molar ratios of BT101. VWF:Act is presented as relative percent concentration which was determined against a curve made from the reference plasma provided with the kit.

At a concentration of 3 μg/mL, BT-200 reduced VWF activity in citrated human plasma to 28.5% of normal (FIG. 4). Incubation of the BT200-treated plasma with increasing molar ratios of BT101 caused a reversal in the BT200-induced reduction in VWF activity, with complete reversal at a 1:1 molar ratio (i.e., the BT200 activity was totally inhibited by BT101, leading to the maximal activity of VWF at the BT200/BT101 molar ratio of 1:1). No further increase as the molar ratio of BT101 to BT200 increased to 2:1. The results demonstrate a dose-dependent increasing of VWF activity in plasma, indicating an inhibition of BT200 activity by BT101.

Example 4: Effect of BT101 on BT200 Induced Inhibition of Platelet Function

The effects of BT101 on BT100 (non-PEGylated version of BT200)-induced inhibition of platelet function were evaluated using a platelet function analyzer (PFA). The PFA assay measures the time required for occlusion of the aperture by platelet plugs, which is defined as closure time (CT). The instrument aspirates a blood sample under constant vacuum from the sample reservoir through a capillary and a microscopic aperture (147 μm) cut into the membrane, which leads to high shear induced platelet plug formation. The membrane is coated with collagen/adenosine diphosphate (CADP), which is very sensitive to VWF levels.

Whole blood samples were incubated with BT-100 (25 or 100 nM) and either saline or 200 nM BT101 at 37° C. for 15 minutes, after which platelet plug formation was measured by collagen/adenosine diphosphate-induced closure time (CADP-CT) with a platelet function analyzer, PFA-100 (Siemens, Marburg, Germany) and compared to an untreated control sample. Maximal CT measured by the PFA-200 is 5 minutes and the instrument gives a result of >300 seconds f this time is exceeded.

Figure 5:
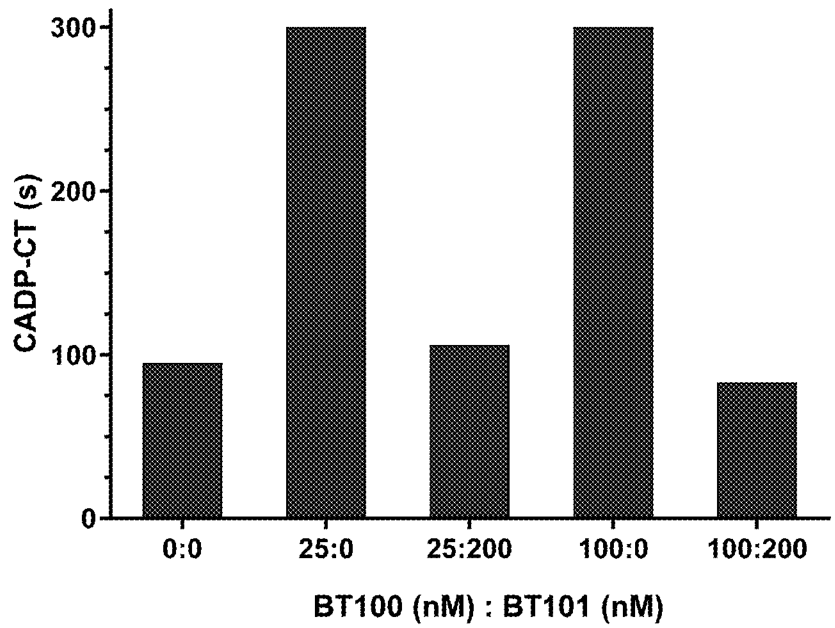
FIG. 5 shows Effects of BT101 on BT100 (SEQ ID NO.: 5; non-PEGylated version of BT200)-induced inhibition of platelet function. Platelet function was assessed as collagen/adenosine diphosphate induced closure time (CADP-CT) in second(s).
Figure 6:
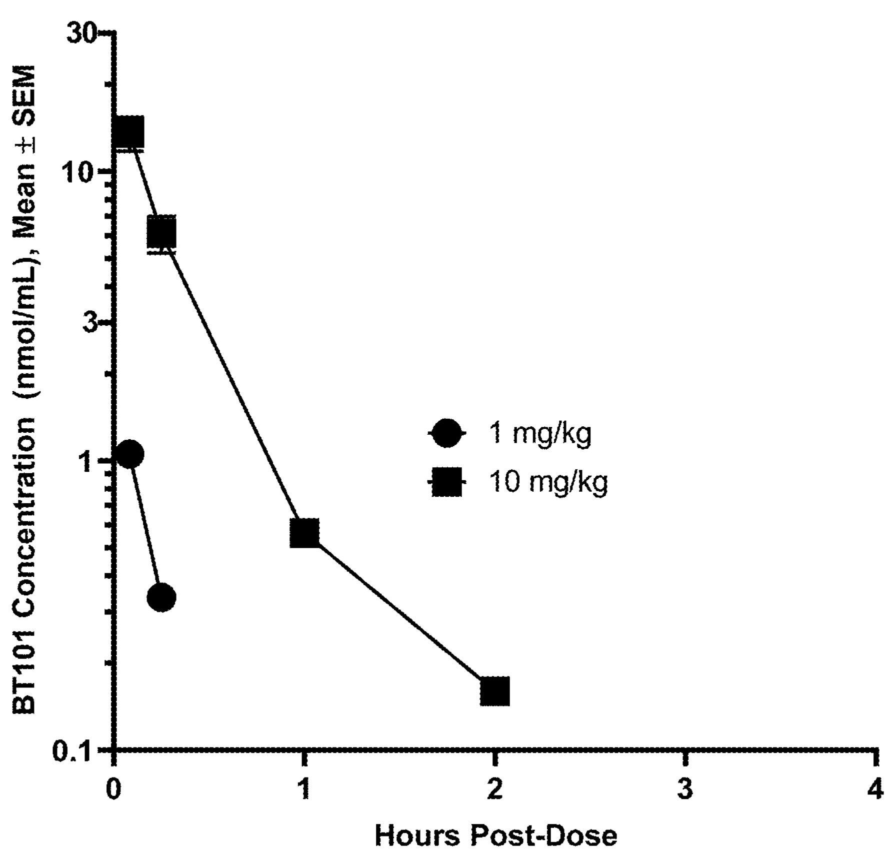
FIG. 6 demonstrates plasma concentrations of BT101 following intravenous administration to male cynomolgus monkey at 1 mg/kg (●) or 10 mg/kg (■). Only time points with concentrations exceeding the limit of quantitation (0.125 nmol/mL) are presented on the graph. Each concentration represents the mean of 3 animals±standard error (SEM).

At a concentration of 3 μg/mL, BT100 reduced VWF activity in citrated human plasma to 28.5% of normal (FIG. 5). Incubation of the BT100-treated plasma with increasing molar ratios of BT101 caused a reversal in the BT100-induced reduction in VWF activity, with complete reversal at a 1:1 molar ratio and no further increase as the molar ratio of BT101 to BT100 increased to 2:1. The test suggested that BT101 reverses the inhibition of platelet function by BT100 in human plasma.

BT101 binds to the core aptamer of BT200 at a 1:1 molar ratio, inhibits BT200 binding to purified human VWF and reverses BT200-induced inhibition of platelet function in vitro.

Example 5: Effects of BT101 of on BT200 Pharmacokinetics and Pharmacodynamics in Cynomolgus Monkey (In Vivo)

The effects of BT101 on BT200 pharmacokinetics and activity were evaluated following intravenous administration to cynomolgus monkeys. Twenty-four hours prior to each BT101 dose, BT200 was administered at a dose level of 0.6 mg/kg (calculated by aptamer/polynucleotide) by subcutaneous injection in 0.9% saline at a dose volume of 1 mL/kg. BT101 was administered intravenously in 0.9% saline at a dose volume of 1 mL/kg at escalating dose levels of 1, 3, and 10 mg/kg. There was a washout period of 21 days between each escalating dose level of BT101.

Pharmacokinetics

Immediately prior to, and at 0.083, 0.25, 1, 2, 4, 8, 24, 48, 168, and 336 hours after each BT101 administration, approximately 1 mL of whole blood was collected from each animal via an anterior cephalic vein into vacutainer tubes containing $K_2EDTA$. Blood samples were mixed gently with the anticoagulant after collection and kept on wet ice until centrifugation at 2000 g for 10 minutes at 4° C. within 1 hour after collection. Approximately 400 μL of plasma was harvested into microcentrifuge tubes which were frozen on dry ice temporarily until transferred to a freezer of approximately −65° C. until analysis for BT101, BT200, and BT-101/BT200 duplex concentrations using an HPLC-UV method with lower limits of quantitation of 0.125 nmol/mL, 0.050 nmol/mL, and 0.125 nmol/mL for BT101, BT200, and BT101/BT200 duplex, respectively.

The concentration-time curve was plotted for each animal for each analyte and the following parameters were calculated using non-compartmental models (WinNonlin 6.3) as data permitted: area under curve from time zero to the last time point with measurable concentration ($AUC_t$), the extrapolated plasma concentration at time 0 ($C_0$), and the elimination half-life ($t_{1/2}$).

Figure 7A:
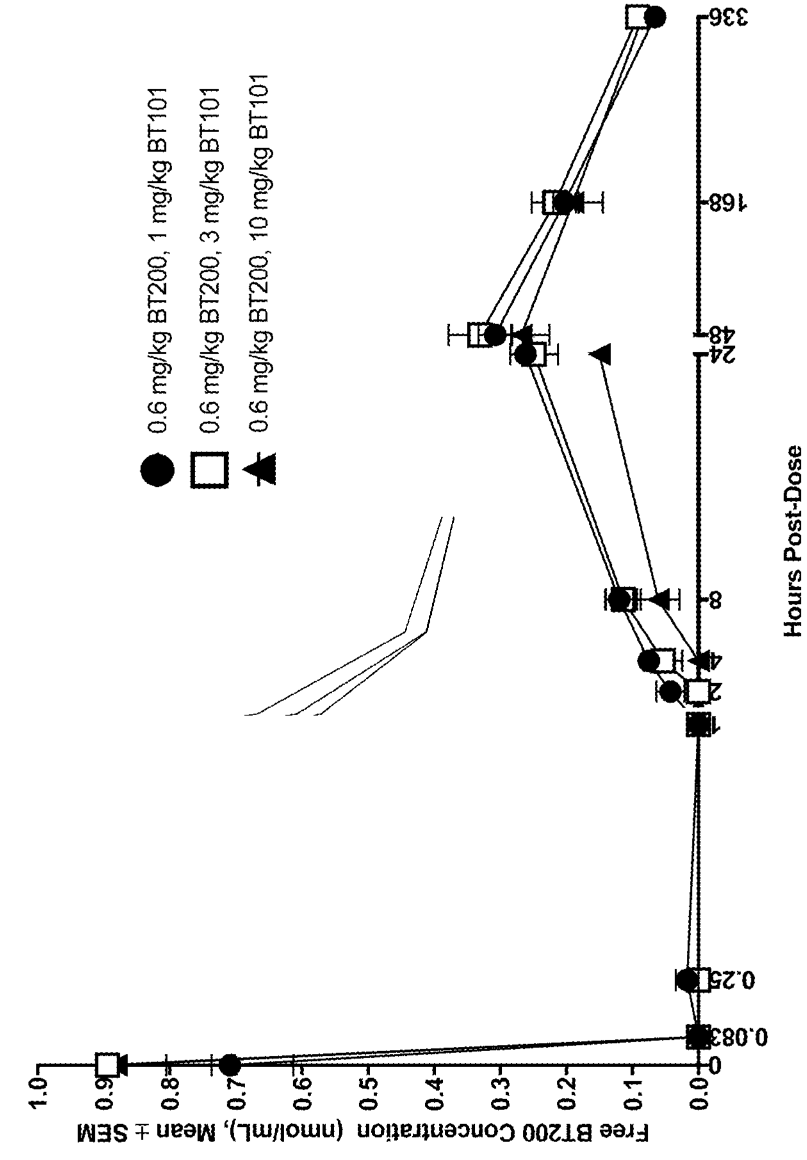
FIGS. 7A-7C shows plasma concentrations of BT200 (7A), BT101/BT200 duplex (7B), and BT101 (7C) after subcutaneous administration of BT200 (0.6 mg/kg) followed 24 hours later by intravenous administration of BT101 at 1 mg/kg (●), 3 mg/kg (u), or 10 mg/kg (▲). For BT101, only time points with concentrations exceeding the limit of quantitation (0.125 nmol/mL) are presented on the graph. Each concentration represents the mean of 3 animals±standard error (SEM).
Figure 7B:
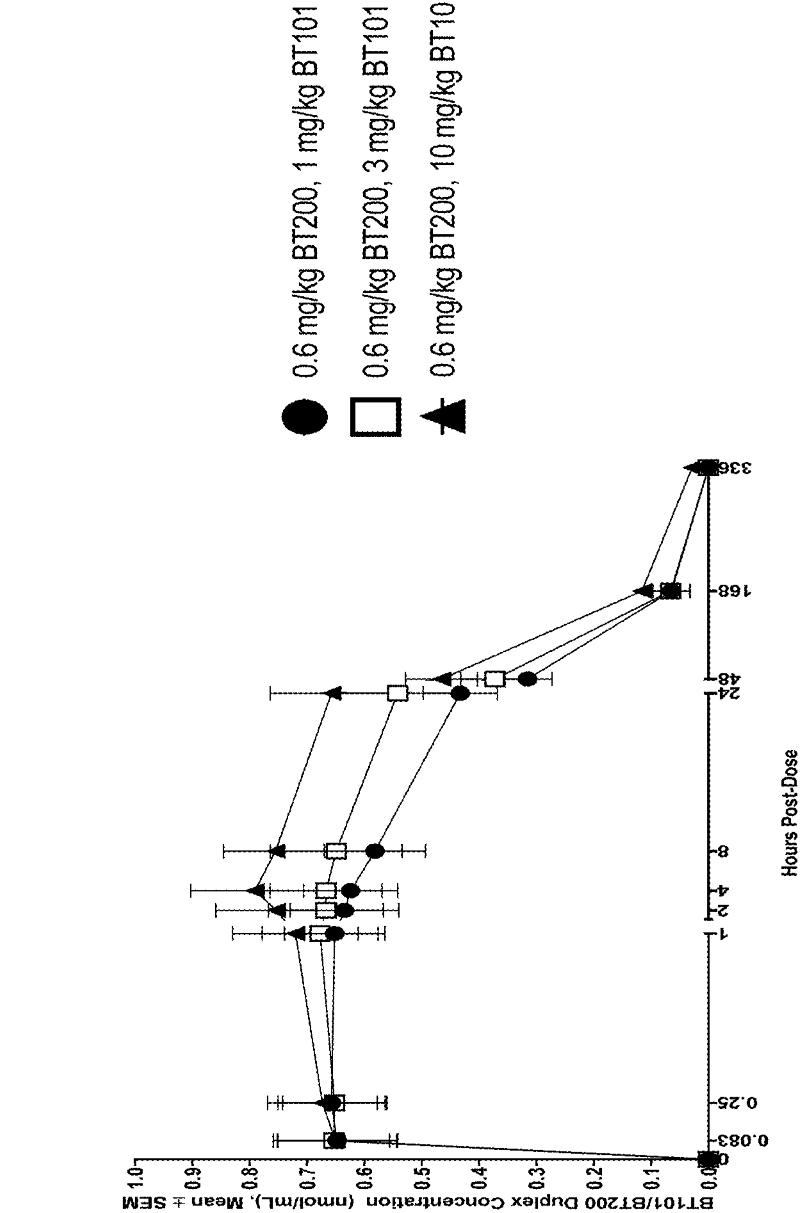
Figure 7C:
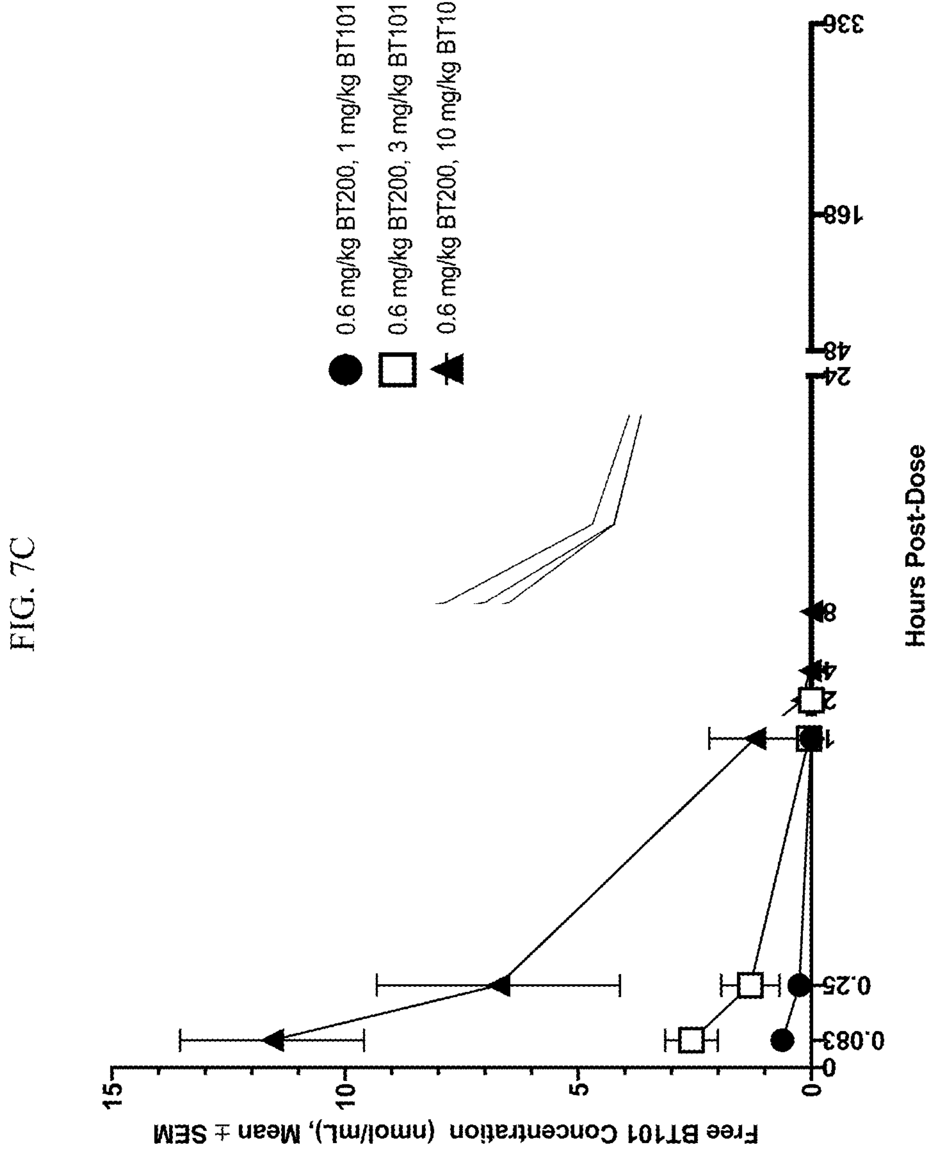

Plasma concentrations of BT200, BT101, and BT101/BT200 duplexes after subcutaneous administration of BT200 followed 24 hours later by intravenous administration of BT101 are shown in FIGS. 7A, 7B and 7C and pharmacokinetic results are summarized in Table 2. At 24 hours following subcutaneous administration of BT200 to cynomolgus monkeys at a dose level of 0.6 mg/kg (calculated by polynucleotide; N=3/group), mean BT200 concentrations ranged from 0.71±0.17 nmol/mL to 0.89±0.33 nmol/mL (Time=0, FIG. 7A). Within 5 minutes (0.083 hours) following intravenous administration of BT101 at dose levels of 1, 3, or 10 mg/kg, BT200 concentrations were below the limit of quantitation (BLQ, <0.05 nmol/mL). At 1 mg/kg BT101, BT200 concentrations remained BLQ for 0.25 hours post-dose after which they slowly increased through 48 hours post-dose. At the higher dose levels of 3 and 10 mg/kg BT-101, BT200 plasma concentrations remained BLQ for 2 and 4 hours, respectively. These decreases in BT200 plasma concentrations coincided with immediate increases in BT101/BT200 duplex concentrations that were noted by 5 minutes following BT101 administration and peaked between 0.44 hours (at 1 mg/kg BT101) and 5.3 hours (at 10 mg/kg BT101) post-dose (FIG. 7B). After achieving peak concentrations, BT101/BT200 duplex concentrations slowly declined through 336 hours following BT101 administration and were BLQ in the 1 and 3 mg/kg dose groups at that time. The mean elimination half-life for BT101/BT200 duplexes ranged from 53.3 to 68.1 hours. BT101 plasma concentrations increased in a dose-related manner from 1 to 10 mg/kg, peaking at 5 minutes following intravenous administration and declining rapidly to BLQ by 1 hour (at 1 mg/kg) to 8 hours (at 10 mg/kg) post-dose (FIG. 7C). Overall, the pharmacokinetic profile of BT101 was similar to that seen following intravenous administration in the absence of BT200 pretreatment, however, slightly lower peak concentrations were noted likely due to the interaction of BT101 with BT200 in the BT101/BT200 duplexes that were formed.

After intravenous administration BT101 was undetectable after 4 hours consistent with the expected short half-life of unconjugated aptamers like BT101 and with the goal of enabling fine control of BT200 activity. Table 3 compare the parameters after administration of BT200, BT101/BT200 duplex and BT101.

TABLE 2

Mean pharmacokinetic parameters following intravenous administration of BT101 to male cynomolgus monkeys (N = 3)

| | Mean ± SD | | | | |
|---|---|---|---|---|---|
| Dose (mg/kg) | $C_0$ (nmol/mL) | $AUC_t$ (nmol*h/mL) | $t_{1/2}$ (hours) | $V_{Z, obs}$ (mg/(nmol/mL)/kg) | $Cl_{obs}$ (mg/(nmol*h/mL)/kg) |
| 1 | 1.05 ± 0.08 | 0.160 ± 0.009 | NC | NC | NC |
| 10 | 13.5 ± 3.15 | 5.06 ± 1.15 | 0.304 ± 0.006 | 0.883 ± 0.196 | 2.01 ± 0.42 |

SD = standard deviation; NC = not calculable due to insufficient number of samples with measurable concentrations.

TABLE 3

Plasma BT200, BT101/BT200 Duplex and BT101 concentrations following subcutaneous administration of BT200 followed by intravenous administration of BT101 to male cynomolgus monkeys

| BT101 Dose | Mean ± SD | | | |
|---|---|---|---|---|
| (mg/kg)[a] | $t_{max}$ (hours)[b] | $C_{max}$ (nmol/mL)[c] | $AUC_t$ (nmol*h/mL) | $t_{1/2}$ (hours)[d] |
| BT200 | | | | |
| 1 | 48 ± 0 | 0.308 ± 0.044 | 63.7 ± 7.60 | 129 ± 13.0 |
| 3 | 48 ± 0 | 0.331 ± 0.082 | 69.1 ± 18.2 | 155 ± 6.09 |
| 10 | 48 ± 0 | 0.270 ± 0.074 | 57.4 ± 18.2 | 181 ± 53.8 |
| BT101/BT200 Duplex | | | | |
| 1 | 0.44 ± 0.49 | 0.670 ± 0.167 | 40.0 ± 20.8 | 56.5 ± 12.3 |
| 3 | 4.3 ± 3.5 | 0.686 ± 0.169 | 46.5 ± 25.0 | 53.3 ± 9.59 |
| 10 | 5.3 ± 2.3 | 0.792 ± 0.192 | 77.9 ± 17.3 | 68.1 ± 3.49 |
| BT101 | | | | |
| 1 | NA | 0.624 ± 0.345 | 0.100 ± 0.061 | NC |
| 3 | NA | 2.57 ± 0.973 | 0.769 ± 0.797 | NC |
| 10 | NA | 11.6 ± 3.42 | 5.88 ± 4.51 | 0.326 ± 0.189 |

[a]The BT-200 dose level for all groups was 0.6 mg/kg (calculated by aptamer/polynucleotide), administered subcutaneously at 24 hours prior to BT101 administration.
[b]Time of maximum plasma concentration following BT101 dosing; NA = not applicable as BT101 was administered intravenously.
[c]For BT200 and BT101/BT200 duplex, maximum plasma concentration following BT101 dosing. For BT101, $C_0$ is provided.
[d]Terminal elimination half-life; NC = not calculable as not calculable due to insufficient number of samples with measurable concentrations in at least 2 of 3 animals.

Evaluation of VWF Activity

VWF Activity was evaluated using the REAADS® test kit. Blood samples were mixed gently with the anticoagulant after collection and kept on wet ice until centrifugation at 2000 g for 10 minutes at 4° C. within 1 hour after collection. Approximately 400 μL of plasma was harvested into micro-centrifuge tubes which were frozen on dry ice temporarily until transferred to a freezer of approximately −65° C. pending analysis for Von Willebrand Factor Activity (VWF: Act) using the REAADS® Von Willebrand Factor activity test kit (Corgenix, Inc.), as discussed in Example 3.

Figure 8:
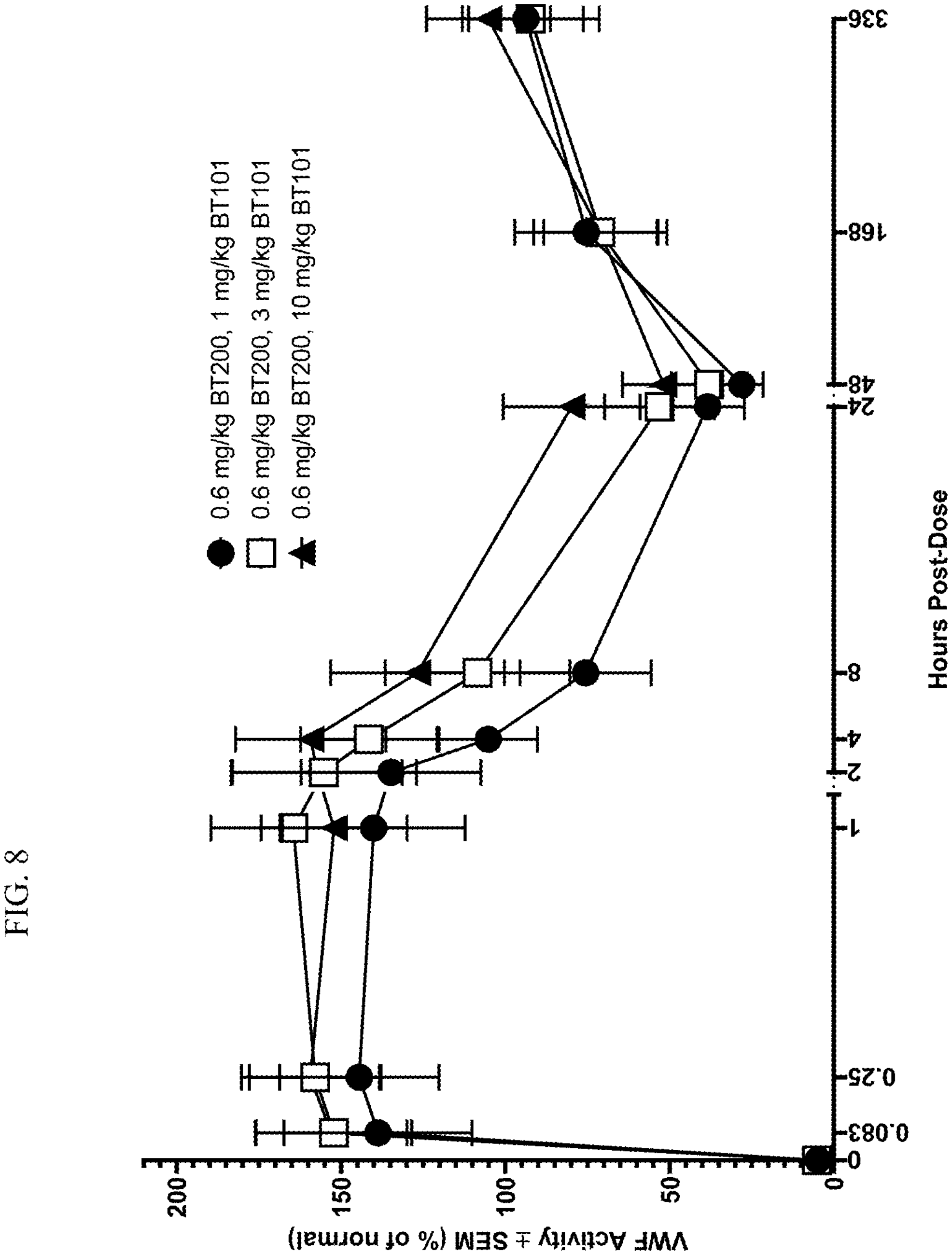
FIG. 8 depicts the VWF activity as measured using the REAADS assay after subcutaneous administration of BT200 (0.6 mg/kg) followed 24 hours later by intravenous administration of BT101 at 1 mg/kg (●), 3 mg/kg (□), or 10 mg/kg (▲). Each value represents the mean of 3 animals±standard error (SEM).

Prior to subcutaneous administration of BT200, mean VWF activity values were 137.4±12.4% (data not shown). At 24 hours following BT-200 administration, mean VWF activity values ranged from 4.9% to 5.4% (Time=0, FIG. 8) indicating that BT-200 significantly inhibited VWF activity at 0.6 mg/kg (calculated by aptamer/polynucleotide). Within 5 minutes following intravenous administration of BT101, the effects of BT200 were reversed and VWF activity values returned to baseline. As with the effects on platelet activity, the onset of the effect on VWF activity correlated with the decline of BT200 plasma concentrations to BLQ values and the appearance of BT101/BT200 duplexes (FIG. 7B). At all dose levels, VWF activities remained near baseline (pre-BT200 administration) values for approximately 2 hours following BT101 administration after which they slowly decreased through 48 hours post-dose with the rate of decrease being dose dependent. From 48 hours to 336 hours post-dose, VWF activity slowly increased consistent with the slow decline in BT200 concentrations (FIG. 7A) during this time period.

Evaluation of Platelet Activity

The effects of BT101 on BT200 induced inhibition of platelet function were evaluated using a using a platelet function analyzer (PFA). The PFA assay measures the time required for occlusion of the aperture by platelet plugs, which is defined as closure time (CT). The instrument aspirates a blood sample under constant vacuum from the sample reservoir through a capillary and a microscopic aperture (147 μm) cut into the membrane, which leads to high shear induced platelet plug formation. The membrane is coated with collagen/adenosine diphosphate (CADP), which is very sensitive to VWF levels.

Immediately prior to, and at 0.083, 0.25, 1, 2, 4, 8, 24, 48, 168, and 336 hours after each BT101 administration, approximately 1 mL of whole blood was collected from each animal via an anterior cephalic vein into vacutainer tubes containing sodium citrate. Blood samples were kept at room temperature and analyzed within 4 hours of sampling. Briefly, after incubation at 37° C. for 15 minutes, platelet plug formation was measured by collagen/adenosine diphosphate-induced closure time (CADP-CT) with a platelet function analyzer, PFA-200 (Siemens, Marburg, Germany). Normal saline was used as a negative control. Maximal CT measured by the PFA-200 is 5 minutes and the instrument gives a result of >300 seconds if this time is exceeded.

Figure 9:
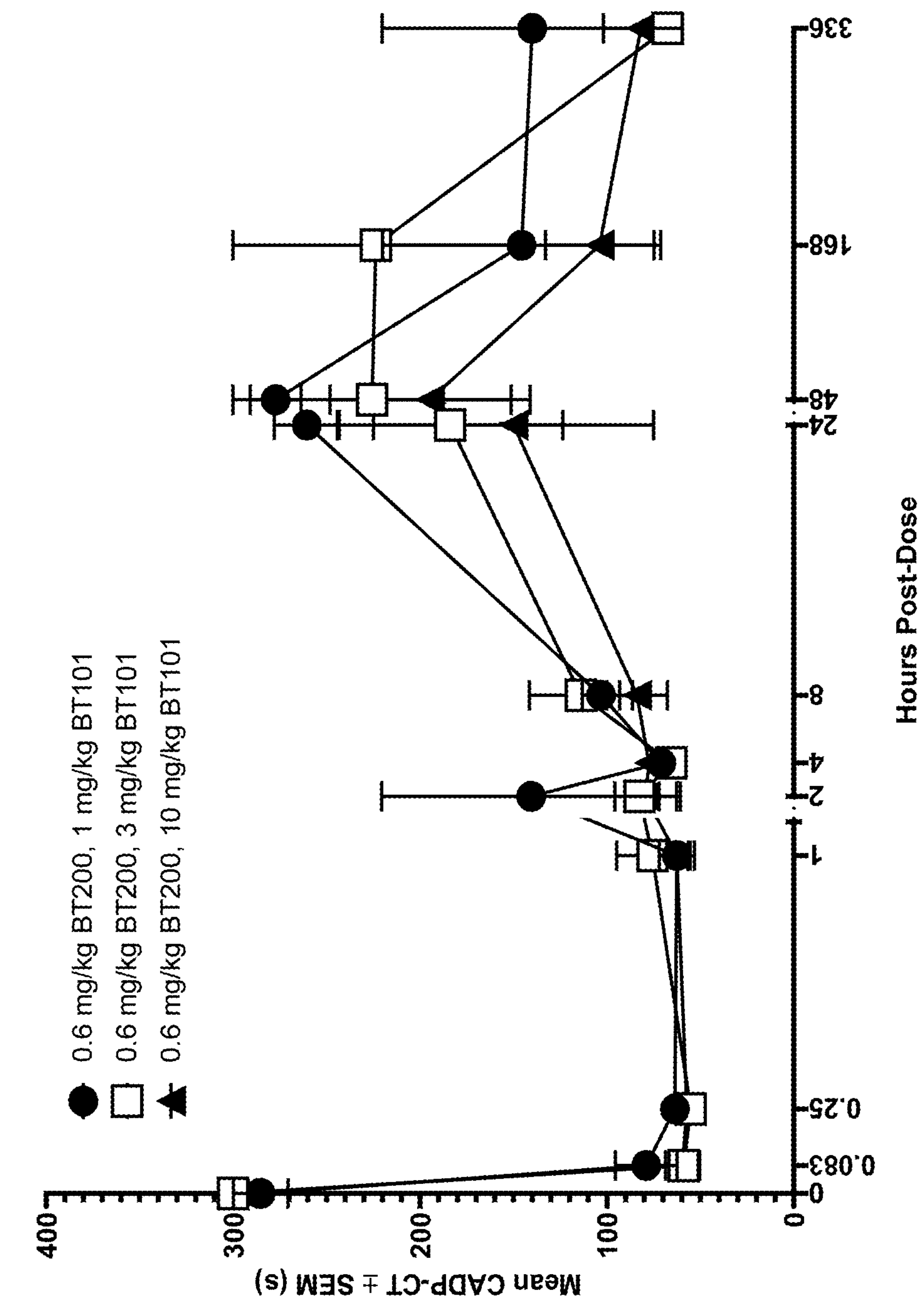
FIG. 9 shows platelet functions as measured by collagen/adenosine diphosphate induced closure time (CADP-CT) in seconds(s) after subcutaneous administration of BT200 (0.6 mg/kg) followed 24 hours later by intravenous administration of BT101 at 1 mg/kg (●), 3 mg/kg (□), or 10 mg/kg (▲). Each value represents the mean of 3 animals±standard error (SEM).

Platelet activity was evaluated by measuring closure time (CADP-CT) using a PFA-200 analyzer. Prior to subcutaneous administration of BT200, mean closure times were 78.3±21.5 seconds (data not shown). At 24 hours following BT200 administration, closure times were at or near the maximum value measured by the PFA-200 of 300 seconds (Time=0; FIG. 9) indicating that BT200 significantly prolonged CADP-CT at 0.6 mg/kg (calculated by aptamer/polynucleotide). Within 5 minutes following intravenous administration of BT101, the effects of BT200 were reversed and closure times returned to baseline values. The onset of the effect correlated with the decline of BT200 plasma concentrations to BLQ values and the appearance of BT101/BT200 duplexes (FIG. 7B). At all dose levels, closure times remained near baseline (pre-BT200 administration) values for approximately 8 hours following BT101 administration after which they slowly increased through 48 hours post-dose before again declining consistent with the peak and then decline in BT200 concentrations (FIG. 7A) during this time period.

Intravenous administration of BT101 reduced BT200 concentrations to below detectable levels through formation of duplexes of BT101 and BT200 and reversed BT200-induced effects on VWF activity and platelet function. These effects of BT101 persisted for 8-24 hours following administration and the duration was dose-dependent. The test of BT200 both in vitro and in vivo without any adverse effects noted in treated animals. results suggest that BT101 effectively reversed the activity

The invention claimed is:

1. A method for treating a clinical condition associated with elevated levels of plasma VWF in a patient comprising: administrating to the patient a VWF binding aptamer comprising the nucleic acid sequence presented by SEQ ID No: 3; and reversing the effect of the VWF binding aptamer using a reversal agent comprising the nucleic acid sequence presented by SEQ ID No: 9, wherein the reversal agent is administered at a ratio of 1:1 relative to the VWF binding aptamer or less in moles when the levels of plasma VWF need to be increased in the patient receiving the treatment of the VWF binding aptamer.

2. The method of claim 1, wherein the clinical condition associated with elevated levels of plasma VWF comprises systemic lupus erythematosus (SLE), first ischemic stroke, secondary stroke, transient ischemic attack (TIA), silent stroke, a cardiovascular disease, diabetic disease, and cancer metastasis.

3. The method of claim 1, wherein the VWF binding aptamer includes at least one nucleotide modification with 2'-O-methyl modification, and wherein the reversal agent includes at least one nucleotide modification with 2'-O-methyl modification.

4. The method of claim 3, wherein the VWF binding aptamer is modified with a conjugate selecting from the group consisting of a PEG polymer, a protein, an antibody or variant thereof, a peptide, a lipid, a fatty acid, a carbohydrate, and a small molecule, and/or wherein the reversal agent is modified with a conjugate selecting from the group consisting of a PEG polymer, a protein, an antibody or variant thereof, a peptide, a lipid, a fatty acid, a carbohydrate, and a small molecule.

5. The method of claim 1, wherein the VWF binding aptamer comprises a nucleic acid sequence selected from the group consisting of SEQ ID Nos: 4-6, and wherein the reversal agent comprises the nucleic acid sequence of SEQ ID No: 10.

6. The method of claim 1 wherein the ratio of the reversal agent and the VWF binding aptamer is, at 1:1.5, at 1:2, at 1:3, at 1:4, or at 1:5 in moles.

7. The method of claim 1, wherein the amount of the reversal agent is administered to reverse the activity of the VWF binding aptamer by 50 to 100%.

8. The method of claim 1, wherein the reversal agent is administered when the patient receiving the treatment of the VWF binding aptamer is under a risk of excessive bleeding.

9. The method of claim 1, wherein the reversal agent is administered when the patient receiving the treatment of the VWF binding aptamer is receiving a clinical surgery.

10. A method of modulating VWF activity in a subject comprising administering to the circulatory system of the subject a VWF binding aptamer having the nucleic acid sequence presented by SEQ ID NO: 3, and reversing the effect of the VWF binding aptamer using a reversal agent having the nucleic acid sequence presented by SEQ ID NO: 9 wherein the reversal agent is used at a ratio of 1:1 to the VWF binding aptamer or less in moles when the activity of plasma VWF needs to be increased.

11. The method of claim 10, wherein the VWF binding aptamer includes at least one nucleotide modification with 2'-O-methyl modification, and wherein the reversal agent includes at least one nucleotide modification with 2'-O-methyl modification.

12. The method of claim 11, wherein the VWF binding aptamer is modified with a conjugate selecting from the group consisting of a PEG polymer, a protein, an antibody or variant thereof, a peptide, a lipid, a fatty acid, a carbohydrate, and a small molecule, and/or wherein the reversal agent is modified with a conjugate selecting from the group consisting of a PEG polymer, a protein, an antibody or variant thereof, a peptide, a lipid, a fatty acid, a carbohydrate, and a small molecule.

13. The method of claim 11, wherein the VWF binding aptamer comprises a nucleic acid sequence selected from the group consisting of SEQ ID Nos: 4-6, and wherein the reversal agent comprises the nucleic acid sequence of SEQ ID No: 10.

14. The method of claim 10, wherein the ratio of the reversal agent and the VWF binding aptamer is, at 1:1.5, at 1:2, at 1:3, at 1:4, or at 1:5 in moles.

15. The method of claim 10, wherein the amount of the reversal agent is used to reverse the activity of the VWF binding aptamer by 50 to 100%.

* * * * *

SEQUENCE LISTING

<160> NUMBER OF SEQ ID NOS: 10

<210> SEQ ID NO 1
<211> LENGTH: 2813
<212> TYPE: PRT
<213> ORGANISM: Homo sapiens

<400> SEQUENCE: 1

Met Ile Pro Ala Arg Phe Ala Gly Val Leu Leu Ala Leu Ala Leu Ile
1 5 10 15

Leu Pro Gly Thr Leu Cys Ala Glu Gly Thr Arg Gly Arg Ser Ser Thr
20 25 30

Ala Arg Cys Ser Leu Phe Gly Ser Asp Phe Val Asn Thr Phe Asp Gly
35 40 45

Ser Met Tyr Ser Phe Ala Gly Tyr Cys Ser Tyr Leu Leu Ala Gly Gly
50 55 60

Cys Gln Lys Arg Ser Phe Ser Ile Ile Gly Asp Phe Gln Asn Gly Lys
65 70 75 80

Arg Val Ser Leu Ser Val Tyr Leu Gly Glu Phe Phe Asp Ile His Leu
85 90 95

Phe Val Asn Gly Thr Val Thr Gln Gly Asp Gln Arg Val Ser Met Pro
100 105 110

Tyr Ala Ser Lys Gly Leu Tyr Leu Glu Thr Glu Ala Gly Tyr Tyr Lys
115 120 125

Leu Ser Gly Glu Ala Tyr Gly Phe Val Ala Arg Ile Asp Gly Ser Gly
130 135 140

Asn Phe Gln Val Leu Leu Ser Asp Arg Tyr Phe Asn Lys Thr Cys Gly
145 150 155 160

Leu Cys Gly Asn Phe Asn Ile Phe Ala Glu Asp Asp Phe Met Thr Gln
165 170 175

Glu Gly Thr Leu Thr Ser Asp Pro Tyr Asp Phe Ala Asn Ser Trp Ala
180 185 190

Leu Ser Ser Gly Glu Gln Trp Cys Glu Arg Ala Ser Pro Pro Ser Ser
195 200 205

Ser Cys Asn Ile Ser Ser Gly Glu Met Gln Lys Gly Leu Trp Glu Gln
210 215 220

Cys Gln Leu Leu Lys Ser Thr Ser Val Phe Ala Arg Cys His Pro Leu
225 230 235 240

Val Asp Pro Glu Pro Phe Val Ala Leu Cys Glu Lys Thr Leu Cys Glu
245 250 255

Cys Ala Gly Gly Leu Glu Cys Ala Cys Pro Ala Leu Leu Glu Tyr Ala
260 265 270

Arg Thr Cys Ala Gln Glu Gly Met Val Leu Tyr Gly Trp Thr Asp His
275 280 285

Ser Ala Cys Ser Pro Val Cys Pro Ala Gly Met Glu Tyr Arg Gln Cys
290 295 300

Val Ser Pro Cys Ala Arg Thr Cys Gln Ser Leu His Ile Asn Glu Met
305 310 315 320

Cys Gln Glu Arg Cys Val Asp Gly Cys Ser Cys Pro Glu Gly Gln Leu
325 330 335

Leu Asp Glu Gly Leu Cys Val Glu Ser Thr Glu Cys Pro Cys Val His
340 345 350

```
Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
```

```
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185
```

```
Thr Cys  Val Asp Pro Glu Asp  Cys Pro Val Cys Glu  Val Ala Gly
    1190                 1195                 1200

Arg Arg  Phe Ala Ser Gly Lys  Lys Val Thr Leu Asn  Pro Ser Asp
    1205                 1210                 1215

Pro Glu  His Cys Gln Ile Cys  His Cys Asp Val Val  Asn Leu Thr
    1220                 1225                 1230

Cys Glu  Ala Cys Gln Glu Pro  Gly Gly Leu Val Val  Pro Pro Thr
    1235                 1240                 1245

Asp Ala  Pro Val Ser Pro Thr  Thr Leu Tyr Val Glu  Asp Ile Ser
    1250                 1255                 1260

Glu Pro  Pro Leu His Asp Phe  Tyr Cys Ser Arg Leu  Leu Asp Leu
    1265                 1270                 1275

Val Phe  Leu Leu Asp Gly Ser  Ser Arg Leu Ser Glu  Ala Glu Phe
    1280                 1285                 1290

Glu Val  Leu Lys Ala Phe Val  Val Asp Met Met Glu  Arg Leu Arg
    1295                 1300                 1305

Ile Ser  Gln Lys Trp Val Arg  Val Ala Val Val Glu  Tyr His Asp
    1310                 1315                 1320

Gly Ser  His Ala Tyr Ile Gly  Leu Lys Asp Arg Lys  Arg Pro Ser
    1325                 1330                 1335

Glu Leu  Arg Arg Ile Ala Ser  Gln Val Lys Tyr Ala  Gly Ser Gln
    1340                 1345                 1350

Val Ala  Ser Thr Ser Glu Val  Leu Lys Tyr Thr Leu  Phe Gln Ile
    1355                 1360                 1365

Phe Ser  Lys Ile Asp Arg Pro  Glu Ala Ser Arg Ile  Thr Leu Leu
    1370                 1375                 1380

Leu Met  Ala Ser Gln Glu Pro  Gln Arg Met Ser Arg  Asn Phe Val
    1385                 1390                 1395

Arg Tyr  Val Gln Gly Leu Lys  Lys Lys Lys Val Ile  Val Ile Pro
    1400                 1405                 1410

Val Gly  Ile Gly Pro His Ala  Asn Leu Lys Gln Ile  Arg Leu Ile
    1415                 1420                 1425

Glu Lys  Gln Ala Pro Glu Asn  Lys Ala Phe Val Leu  Ser Ser Val
    1430                 1435                 1440

Asp Glu  Leu Glu Gln Gln Arg  Asp Glu Ile Val Ser  Tyr Leu Cys
    1445                 1450                 1455

Asp Leu  Ala Pro Glu Ala Pro  Pro Pro Thr Leu Pro  Pro Asp Met
    1460                 1465                 1470

Ala Gln  Val Thr Val Gly Pro  Gly Leu Leu Gly Val  Ser Thr Leu
    1475                 1480                 1485

Gly Pro  Lys Arg Asn Ser Met  Val Leu Asp Val Ala  Phe Val Leu
    1490                 1495                 1500

Glu Gly  Ser Asp Lys Ile Gly  Glu Ala Asp Phe Asn  Arg Ser Lys
    1505                 1510                 1515

Glu Phe  Met Glu Glu Val Ile  Gln Arg Met Asp Val  Gly Gln Asp
    1520                 1525                 1530

Ser Ile  His Val Thr Val Leu  Gln Tyr Ser Tyr Met  Val Thr Val
    1535                 1540                 1545

Glu Tyr  Pro Phe Ser Glu Ala  Gln Ser Lys Gly Asp  Ile Leu Gln
    1550                 1555                 1560

Arg Val  Arg Glu Ile Arg Tyr  Gln Gly Gly Asn Arg  Thr Asn Thr
    1565                 1570                 1575
```

```
Gly Leu Ala Leu Arg Tyr Leu Ser Asp His Ser Phe Leu Val Ser
    1580                1585                1590

Gln Gly Asp Arg Glu Gln Ala Pro Asn Leu Val Tyr Met Val Thr
    1595                1600                1605

Gly Asn Pro Ala Ser Asp Glu Ile Lys Arg Leu Pro Gly Asp Ile
    1610                1615                1620

Gln Val Val Pro Ile Gly Val Gly Pro Asn Ala Asn Val Gln Glu
    1625                1630                1635

Leu Glu Arg Ile Gly Trp Pro Asn Ala Pro Ile Leu Ile Gln Asp
    1640                1645                1650

Phe Glu Thr Leu Pro Arg Glu Ala Pro Asp Leu Val Leu Gln Arg
    1655                1660                1665

Cys Cys Ser Gly Glu Gly Leu Gln Ile Pro Thr Leu Ser Pro Ala
    1670                1675                1680

Pro Asp Cys Ser Gln Pro Leu Asp Val Ile Leu Leu Leu Asp Gly
    1685                1690                1695

Ser Ser Ser Phe Pro Ala Ser Tyr Phe Asp Glu Met Lys Ser Phe
    1700                1705                1710

Ala Lys Ala Phe Ile Ser Lys Ala Asn Ile Gly Pro Arg Leu Thr
    1715                1720                1725

Gln Val Ser Val Leu Gln Tyr Gly Ser Ile Thr Thr Ile Asp Val
    1730                1735                1740

Pro Trp Asn Val Val Pro Glu Lys Ala His Leu Leu Ser Leu Val
    1745                1750                1755

Asp Val Met Gln Arg Glu Gly Gly Pro Ser Gln Ile Gly Asp Ala
    1760                1765                1770

Leu Gly Phe Ala Val Arg Tyr Leu Thr Ser Glu Met His Gly Ala
    1775                1780                1785

Arg Pro Gly Ala Ser Lys Ala Val Val Ile Leu Val Thr Asp Val
    1790                1795                1800

Ser Val Asp Ser Val Asp Ala Ala Ala Asp Ala Ala Arg Ser Asn
    1805                1810                1815

Arg Val Thr Val Phe Pro Ile Gly Ile Gly Asp Arg Tyr Asp Ala
    1820                1825                1830

Ala Gln Leu Arg Ile Leu Ala Gly Pro Ala Gly Asp Ser Asn Val
    1835                1840                1845

Val Lys Leu Gln Arg Ile Glu Asp Leu Pro Thr Met Val Thr Leu
    1850                1855                1860

Gly Asn Ser Phe Leu His Lys Leu Cys Ser Gly Phe Val Arg Ile
    1865                1870                1875

Cys Met Asp Glu Asp Gly Asn Glu Lys Arg Pro Gly Asp Val Trp
    1880                1885                1890

Thr Leu Pro Asp Gln Cys His Thr Val Thr Cys Gln Pro Asp Gly
    1895                1900                1905

Gln Thr Leu Leu Lys Ser His Arg Val Asn Cys Asp Arg Gly Leu
    1910                1915                1920

Arg Pro Ser Cys Pro Asn Ser Gln Ser Pro Val Lys Val Glu Glu
    1925                1930                1935

Thr Cys Gly Cys Arg Trp Thr Cys Pro Cys Val Cys Thr Gly Ser
    1940                1945                1950

Ser Thr Arg His Ile Val Thr Phe Asp Gly Gln Asn Phe Lys Leu
    1955                1960                1965

Thr Gly Ser Cys Ser Tyr Val Leu Phe Gln Asn Lys Glu Gln Asp
```

```
    1970                1975                1980

Leu Glu  Val Ile Leu His Asn  Gly Ala Cys Ser Pro  Gly Ala Arg
    1985                1990                1995

Gln Gly  Cys Met Lys Ser Ile  Glu Val Lys His Ser  Ala Leu Ser
    2000                2005                2010

Val Glu  Leu His Ser Asp Met  Glu Val Thr Val Asn  Gly Arg Leu
    2015                2020                2025

Val Ser  Val Pro Tyr Val Gly  Gly Asn Met Glu Val  Asn Val Tyr
    2030                2035                2040

Gly Ala  Ile Met His Glu Val  Arg Phe Asn His Leu  Gly His Ile
    2045                2050                2055

Phe Thr  Phe Thr Pro Gln Asn  Asn Glu Phe Gln Leu  Gln Leu Ser
    2060                2065                2070

Pro Lys  Thr Phe Ala Ser Lys  Thr Tyr Gly Leu Cys  Gly Ile Cys
    2075                2080                2085

Asp Glu  Asn Gly Ala Asn Asp  Phe Met Leu Arg Asp  Gly Thr Val
    2090                2095                2100

Thr Thr  Asp Trp Lys Thr Leu  Val Gln Glu Trp Thr  Val Gln Arg
    2105                2110                2115

Pro Gly  Gln Thr Cys Gln Pro  Ile Leu Glu Glu Gln  Cys Leu Val
    2120                2125                2130

Pro Asp  Ser Ser His Cys Gln  Val Leu Leu Leu Pro  Leu Phe Ala
    2135                2140                2145

Glu Cys  His Lys Val Leu Ala  Pro Ala Thr Phe Tyr  Ala Ile Cys
    2150                2155                2160

Gln Gln  Asp Ser Cys His Gln  Glu Gln Val Cys Glu  Val Ile Ala
    2165                2170                2175

Ser Tyr  Ala His Leu Cys Arg  Thr Asn Gly Val Cys  Val Asp Trp
    2180                2185                2190

Arg Thr  Pro Asp Phe Cys Ala  Met Ser Cys Pro Pro  Ser Leu Val
    2195                2200                2205

Tyr Asn  His Cys Glu His Gly  Cys Pro Arg His Cys  Asp Gly Asn
    2210                2215                2220

Val Ser  Ser Cys Gly Asp His  Pro Ser Glu Gly Cys  Phe Cys Pro
    2225                2230                2235

Pro Asp  Lys Val Met Leu Glu  Gly Ser Cys Val Pro  Glu Glu Ala
    2240                2245                2250

Cys Thr  Gln Cys Ile Gly Glu  Asp Gly Val Gln His  Gln Phe Leu
    2255                2260                2265

Glu Ala  Trp Val Pro Asp His  Gln Pro Cys Gln Ile  Cys Thr Cys
    2270                2275                2280

Leu Ser  Gly Arg Lys Val Asn  Cys Thr Thr Gln Pro  Cys Pro Thr
    2285                2290                2295

Ala Lys  Ala Pro Thr Cys Gly  Leu Cys Glu Val Ala  Arg Leu Arg
    2300                2305                2310

Gln Asn  Ala Asp Gln Cys Cys  Pro Glu Tyr Glu Cys  Val Cys Asp
    2315                2320                2325

Pro Val  Ser Cys Asp Leu Pro  Pro Val Pro His Cys  Glu Arg Gly
    2330                2335                2340

Leu Gln  Pro Thr Leu Thr Asn  Pro Gly Glu Cys Arg  Pro Asn Phe
    2345                2350                2355

Thr Cys  Ala Cys Arg Lys Glu  Glu Cys Lys Arg Val  Ser Pro Pro
    2360                2365                2370
```

```
Ser Cys  Pro Pro His Arg Leu  Pro Thr Leu Arg Lys  Thr Gln Cys
    2375                 2380                 2385

Cys Asp  Glu Tyr Glu Cys Ala  Cys Asn Cys Val Asn  Ser Thr Val
    2390                 2395                 2400

Ser Cys  Pro Leu Gly Tyr Leu  Ala Ser Thr Ala Thr  Asn Asp Cys
    2405                 2410                 2415

Gly Cys  Thr Thr Thr Thr Cys  Leu Pro Asp Lys Val  Cys Val His
    2420                 2425                 2430

Arg Ser  Thr Ile Tyr Pro Val  Gly Gln Phe Trp Glu  Glu Gly Cys
    2435                 2440                 2445

Asp Val  Cys Thr Cys Thr Asp  Met Glu Asp Ala Val  Met Gly Leu
    2450                 2455                 2460

Arg Val  Ala Gln Cys Ser Gln  Lys Pro Cys Glu Asp  Ser Cys Arg
    2465                 2470                 2475

Ser Gly  Phe Thr Tyr Val Leu  His Glu Gly Glu Cys  Cys Gly Arg
    2480                 2485                 2490

Cys Leu  Pro Ser Ala Cys Glu  Val Val Thr Gly Ser  Pro Arg Gly
    2495                 2500                 2505

Asp Ser  Gln Ser Ser Trp Lys  Ser Val Gly Ser Gln  Trp Ala Ser
    2510                 2515                 2520

Pro Glu  Asn Pro Cys Leu Ile  Asn Glu Cys Val Arg  Val Lys Glu
    2525                 2530                 2535

Glu Val  Phe Ile Gln Gln Arg  Asn Val Ser Cys Pro  Gln Leu Glu
    2540                 2545                 2550

Val Pro  Val Cys Pro Ser Gly  Phe Gln Leu Ser Cys  Lys Thr Ser
    2555                 2560                 2565

Ala Cys  Cys Pro Ser Cys Arg  Cys Glu Arg Met Glu  Ala Cys Met
    2570                 2575                 2580

Leu Asn  Gly Thr Val Ile Gly  Pro Gly Lys Thr Val  Met Ile Asp
    2585                 2590                 2595

Val Cys  Thr Thr Cys Arg Cys  Met Val Gln Val Gly  Val Ile Ser
    2600                 2605                 2610

Gly Phe  Lys Leu Glu Cys Arg  Lys Thr Thr Cys Asn  Pro Cys Pro
    2615                 2620                 2625

Leu Gly  Tyr Lys Glu Glu Asn  Asn Thr Gly Glu Cys  Cys Gly Arg
    2630                 2635                 2640

Cys Leu  Pro Thr Ala Cys Thr  Ile Gln Leu Arg Gly  Gly Gln Ile
    2645                 2650                 2655

Met Thr  Leu Lys Arg Asp Glu  Thr Leu Gln Asp Gly  Cys Asp Thr
    2660                 2665                 2670

His Phe  Cys Lys Val Asn Glu  Arg Gly Glu Tyr Phe  Trp Glu Lys
    2675                 2680                 2685

Arg Val  Thr Gly Cys Pro Pro  Phe Asp Glu His Lys  Cys Leu Ala
    2690                 2695                 2700

Glu Gly  Gly Lys Ile Met Lys  Ile Pro Gly Thr Cys  Cys Asp Thr
    2705                 2710                 2715

Cys Glu  Glu Pro Glu Cys Asn  Asp Ile Thr Ala Arg  Leu Gln Tyr
    2720                 2725                 2730

Val Lys  Val Gly Ser Cys Lys  Ser Glu Val Glu Val  Asp Ile His
    2735                 2740                 2745

Tyr Cys  Gln Gly Lys Cys Ala  Ser Lys Ala Met Tyr  Ser Ile Asp
    2750                 2755                 2760
```

```
Ile Asn  Asp Val Gln Asp Gln  Cys Ser Cys Cys Ser  Pro Thr Arg
    2765                 2770                 2775

Thr Glu  Pro Met Gln Val Ala  Leu His Cys Thr Asn  Gly Ser Val
    2780                 2785                 2790

Val Tyr  His Glu Val Leu Asn  Ala Met Glu Cys Lys  Cys Ser Pro
    2795                 2800                 2805

Arg Lys  Cys Ser Lys
    2810


<210> SEQ ID NO 2
<211> LENGTH: 8833
<212> TYPE: DNA
<213> ORGANISM: Homo sapiens

<400> SEQUENCE: 2

agctcacagc tattgtggtg ggaaagggag ggtggttggt ggatgtcaca gcttgggctt     60

tatctccccc agcagtgggg actccacagc ccctgggcta cataacagca agacagtccg    120

gagctgtagc agacctgatt gagcctttgc agcagctgag agcatggcct agggtgggcg    180

gcaccattgt ccagcagctg agtttcccag ggaccttgga gatagccgca gccctcattt    240

gcaggggaag atgattcctg ccagatttgc cggggtgctg cttgctctgg ccctcatttt    300

gccagggacc ctttgtgcag aaggaactcg cggcaggtca tccacggccc gatgcagcct    360

tttcggaagt gacttcgtca acacctttga tgggagcatg tacagctttg cgggatactg    420

cagttacctc ctggcagggg gctgccagaa acgctccttc tcgattattg gggacttcca    480

gaatggcaag agagtgagcc tctccgtgta tcttggggaa ttttttgaca tccatttgtt    540

tgtcaatggt accgtgacac agggggacca aagagtctcc atgccctatg cctccaaagg    600

gctgtatcta gaaactgagg ctgggtacta caagctgtcc ggtgaggcct atggctttgt    660

ggccaggatc gatggcagcg gcaactttca agtcctgctg tcagacagat acttcaacaa    720

gacctgcggg ctgtgtggca actttaacat ctttgctgaa gatgacttta tgacccaaga    780

agggaccttg acctcggacc cttatgactt tgccaactca tgggctctga gcagtggaga    840

acagtggtgt gaacgggcat ctcctcccag cagctcatgc aacatctcct ctggggaaat    900

gcagaagggc ctgtgggagc agtgccagct tctgaagagc acctcggtgt ttgcccgctg    960

ccaccctctg gtggaccccg agccttttgt ggccctgtgt gagaagactt tgtgtgagtg   1020

tgctgggggg ctggagtgcg cctgccctgc cctcctggag tacgcccgga cctgtgccca   1080

ggagggaatg gtgctgtacg gctggaccga ccacagcgcg tgcagcccag tgtgccctgc   1140

tggtatggag tataggcagt gtgtgtcccc ttgcgccagg acctgccaga gcctgcacat   1200

caatgaaatg tgtcaggagc gatgcgtgga tggctgcagc tgccctgagg gacagctcct   1260

ggatgaaggc ctctgcgtgg agagcaccga gtgtccctgc gtgcattccg gaaagcgcta   1320

ccctcccggc acctccctct ctcgagactg caacacctgc atttgccgaa acagccagtg   1380

gatctgcagc aatgaagaat gtccagggga gtgccttgtc acaggtcaat cacacttcaa   1440

gagctttgac aacagatact tcaccttcag tgggatctgc cagtacctgc tggcccggga   1500

ttgccaggac cactccttct ccattgtcat tgagactgtc cagtgtgctg atgaccgcga   1560

cgctgtgtgc acccgctccg tcaccgtccg gctgcctggc ctgcacaaca gccttgtgaa   1620

actgaagcat ggggcaggag ttgccatgga tggccaggac gtccagctcc ccctcctgaa   1680

aggtgacctc cgcatccagc atacagtgac ggcctccgtg cgcctcagct acggggagga   1740

cctgcagatg gactgggatg gccgcgggag gctgctggtg aagctgtccc ccgtctatgc   1800
```

```
cgggaagacc tgcggcctgt gtgggaatta caatggcaac cagggcgacg acttccttac   1860
cccctctggg ctggcggagc cccgggtgga ggacttcggg aacgcctgga agctgcacgg   1920
ggactgccag gacctgcaga agcagcacag cgatccctgc gccctcaacc cgcgcatgac   1980
caggttctcc gaggaggcgt gcgcggtcct gacgtccccc acattcgagg cctgccatcg   2040
tgccgtcagc ccgctgccct acctgcggaa ctgccgctac gacgtgtgct cctgctcgga   2100
cggccgcgag tgcctgtgcg gcgccctggc cagctatgcc gcggcctgcg cggggagagg   2160
cgtgcgcgtc gcgtggcgcg agccaggccg ctgtgagctg aactgcccga aaggccaggt   2220
gtacctgcag tgcgggaccc cctgcaacct gacctgccgc tctctctctt acccggatga   2280
ggaatgcaat gaggcctgcc tggagggctg cttctgcccc ccagggctct acatggatga   2340
gaggggggac tgcgtgccca aggcccagtg cccctgttac tatgacggtg agatcttcca   2400
gccagaagac atcttctcag accatcacac catgtgctac tgtgaggatg gcttcatgca   2460
ctgtaccatg agtggagtcc ccggaagctt gctgcctgac gctgtcctca gcagtcccct   2520
gtctcatcgc agcaaaagga gcctatcctg tcggcccccc atggtcaagc tggtgtgtcc   2580
cgctgacaac ctgcgggctg aagggctcga gtgtaccaaa acgtgccaga actatgacct   2640
ggagtgcatg agcatgggct gtgtctctgg ctgcctctgc cccccgggca tggtccggca   2700
tgagaacaga tgtgtggccc tggaaaggtg tccctgcttc catcagggca aggagtatgc   2760
ccctggagaa acagtgaaga ttggctgcaa cacttgtgtc tgtcgggacc ggaagtggaa   2820
ctgcacagac catgtgtgtg atgccacgtg ctccacgatc ggcatggccc actacctcac   2880
cttcgacggg ctcaaatacc tgttccccgg ggagtgccag tacgttctgg tgcaggatta   2940
ctgcggcagt aaccctggga cctttcggat cctagtgggg aataagggat gcagccaccc   3000
ctcagtgaaa tgcaagaaac gggtcaccat cctggtggag ggaggagaga ttgagctgtt   3060
tgacggggag gtgaatgtga agaggcccat gaaggatgag actcactttg aggtggtgga   3120
gtctggccgg tacatcattc tgctgctggg caaagccctc tccgtggtct gggaccgcca   3180
cctgagcatc tccgtggtcc tgaagcagac ataccaggag aaagtgtgtg gcctgtgtgg   3240
gaattttgat ggcatccaga acaatgacct caccagcagc aacctccaag tggaggaaga   3300
ccctgtggac tttgggaact cctggaaagt gagctcgcag tgtgctgaca ccagaaaagt   3360
gcctctggac tcatcccctg ccacctgcca taacaacatc atgaagcaga cgatggtgga   3420
ttcctcctgt agaatcctta ccagtgacgt cttccaggac tgcaacaagc tggtggaccc   3480
cgagccatat ctggatgtct gcatttacga cacctgctcc tgtgagtcca ttggggactg   3540
cgcctgcttc tgcgacacca ttgctgccta tgcccacgtg tgtgcccagc atggcaaggt   3600
ggtgacctgg aggacggcca cattgtgccc ccagagctgc gaggagagga atctccggga   3660
gaacgggtat gagtgtgagt ggcgctataa cagctgtgca cctgcctgtc aagtcacgtg   3720
tcagcaccct gagccactgg cctgccctgt gcagtgtgtg gagggctgcc atgcccactg   3780
ccctccaggg aaaatcctgg atgagctttt gcagacctgc gttgaccctg aagactgtcc   3840
agtgtgtgag gtggctggcc ggcgttttgc ctcaggaaag aaagtcacct tgaatcccag   3900
tgaccctgag cactgccaga tttgccactg tgatgttgtc aacctcacct gtgaagcctg   3960
ccaggagccg ggaggcctgg tggtgcctcc cacagatgcc ccggtgagcc ccaccactct   4020
gtatgtggag gacatctcgg aaccgccgtt gcacgatttc tactgcagca ggctactgga   4080
cctggtcttc ctgctggatg gctcctccag gctgtccgag gctgagtttg aagtgctgaa   4140
```

```
ggcctttgtg gtggacatga tggagcggct gcgcatctcc cagaagtggg tccgcgtggc   4200
cgtggtggag taccacgacg gctcccacgc ctacatcggg ctcaaggacc ggaagcgacc   4260
gtcagagctg cggcgcattg ccagccaggt gaagtatgcg ggcagccagg tggcctccac   4320
cagcgaggtc ttgaaataca cactgttcca aatcttcagc aagatcgacc gccctgaagc   4380
ctcccgcatc accctgctcc tgatggccag ccaggagccc caacggatgt cccggaactt   4440
tgtccgctac gtccagggcc tgaagaagaa gaaggtcatt gtgatcccgg tgggcattgg   4500
gccccatgcc aacctcaagc agatccgcct catcgagaag caggcccctg agaacaaggc   4560
cttcgtgctg agcagtgtgg atgagctgga gcagcaaagg gacgagatcg ttagctacct   4620
ctgtgacctt gcccctgaag cccctcctcc tactctgccc cccgacatgg cacaagtcac   4680
tgtgggcccg gggctcttgg gggtttcgac cctggggccc aagaggaact ccatggttct   4740
ggatgtggcg ttcgtcctgg aaggatcgga caaaattggt gaagccgact tcaacaggag   4800
caaggagttc atggaggagg tgattcagcg gatggatgtg ggccaggaca gcatccacgt   4860
cacggtgctg cagtactcct acatggtgac tgtggagtac cccttcagcg aggcacagtc   4920
caaaggggac atcctgcagc gggtgcgaga gatccgctac cagggcggca acaggaccaa   4980
cactgggctg gccctgcggt acctctctga ccacagcttc ttggtcagcc agggtgaccg   5040
ggagcaggcg cccaacctgg tctacatggt caccggaaat cctgcctctg atgagatcaa   5100
gaggctgcct ggagacatcc aggtggtgcc cattggagtg ggccctaatg ccaacgtgca   5160
ggagctggag aggattggct ggcccaatgc ccctatcctc atccaggact ttgagacgct   5220
cccccgagag gctcctgacc tggtgctgca gaggtgctgc tccggagagg ggctgcagat   5280
ccccaccctc tcccctgcac ctgactgcag ccagcccctg gacgtgatcc ttctcctgga   5340
tggctcctcc agtttcccag cttcttattt tgatgaaatg aagagtttcg ccaaggcttt   5400
catttcaaaa gccaatatag ggcctcgtct cactcaggtg tcagtgctgc agtatggaag   5460
catcaccacc attgacgtgc catggaacgt ggtcccggag aaagcccatt tgctgagcct   5520
tgtggacgtc atgcagcggg agggaggccc cagccaaatc ggggatgcct tgggctttgc   5580
tgtgcgatac ttgacttcag aaatgcatgg tgccaggccg ggagcctcaa aggcggtggt   5640
catcctggtc acggacgtct ctgtggattc agtggatgca gcagctgatg ccgccaggtc   5700
caacagagtg acagtgttcc ctattggaat tggagatcgc tacgatgcag cccagctacg   5760
gatcttggca ggcccagcag gcgactccaa cgtggtgaag ctccagcgaa tcgaagacct   5820
ccctaccatg gtcaccttgg gcaattcctt cctccacaaa ctgtgctctg gatttgttag   5880
gatttgcatg gatgaggatg ggaatgagaa gaggcccggg gacgtctgga ccttgccaga   5940
ccagtgccac accgtgactt gccagccaga tggccagacc ttgctgaaga gtcatcgggt   6000
caactgtgac cgggggctga ggccttcgtg ccctaacagc cagtcccctg ttaaagtgga   6060
agagacctgt ggctgccgct ggacctgccc ctgcgtgtgc acaggcagct ccactcggca   6120
catcgtgacc tttgatgggc agaatttcaa gctgactggc agctgttctt atgtcctatt   6180
tcaaaacaag gagcaggacc tggaggtgat tctccataat ggtgcctgca gccctggagc   6240
aaggcagggc tgcatgaaat ccatcgaggt gaagcacagt gccctctccg tcgagctgca   6300
cagtgacatg gaggtgacgg tgaatgggag actggtctct gttccttacg tgggtgggaa   6360
catggaagtc aacgtttatg gtgccatcat gcatgaggtc agattcaatc accttggtca   6420
catcttcaca ttcactccac aaaacaatga gttccaactg cagctcagcc ccaagacttt   6480
tgcttcaaag acgtatggtc tgtgtgggat ctgtgatgag aacggagcca atgacttcat   6540
```

```
gctgagggat ggcacagtca ccacagactg gaaaacactt gttcaggaat ggactgtgca   6600
gcggccaggg cagacgtgcc agcccatcct ggaggagcag tgtcttgtcc ccgacagctc   6660
ccactgccag gtcctcctct taccactgtt tgctgaatgc cacaaggtcc tggctccagc   6720
cacattctat gccatctgcc agcaggacag ttgccaccag gagcaagtgt gtgaggtgat   6780
cgcctcttat gcccacctct gtcggaccaa cggggtctgc gttgactgga ggacacctga   6840
tttctgtgct atgtcatgcc caccatctct ggtctacaac cactgtgagc atggctgtcc   6900
ccggcactgt gatggcaacg tgagctcctg tggggaccat ccctccgaag gctgtttctg   6960
ccctccagat aaagtcatgt tggaaggcag ctgtgtccct gaagaggcct gcactcagtg   7020
cattggtgag gatggagtcc agcaccagtt cctggaagcc tgggtcccgg accaccagcc   7080
ctgtcagatc tgcacatgcc tcagcgggcg gaaggtcaac tgcacaacgc agccctgccc   7140
cacggccaaa gctcccacgt gtggcctgtg tgaagtagcc cgcctccgcc agaatgcaga   7200
ccagtgctgc cccgagtatg agtgtgtgtg tgacccagtg agctgtgacc tgcccccagt   7260
gcctcactgt gaacgtggcc tccagcccac actgaccaac cctggcgagt gcagacccaa   7320
cttcacctgc gcctgcagga aggaggagtg caaaagagtg tccccaccct cctgcccccc   7380
gcaccgtttg cccacccttc ggaagaccca gtgctgtgat gagtatgagt gtgcctgcaa   7440
ctgtgtcaac tccacagtga gctgtcccct tgggtacttg gcctcaactg ccaccaatga   7500
ctgtggctgt accacaacca cctgccttcc cgacaaggtg tgtgtccacc gaagcaccat   7560
ctaccctgtg ggccagttct gggaggaggg ctgcgatgtg tgcacctgca ccgacatgga   7620
ggatgccgtg atgggcctcc gcgtggccca gtgctcccag aagccctgtg aggacagctg   7680
tcggtcgggc ttcacttacg ttctgcatga aggcgagtgc tgtggaaggt gcctgccatc   7740
tgcctgtgag gtggtgactg gctcaccgcg gggggactcc cagtcttcct ggaagagtgt   7800
cggctcccag tgggcctccc cggagaaccc ctgcctcatc aatgagtgtg tccgagtgaa   7860
ggaggaggtc tttatacaac aaaggaacgt ctcctgcccc cagctggagg tccctgtctg   7920
cccctcgggc tttcagctga gctgtaagac ctcagcgtgc tgcccaagct gtcgctgtga   7980
gcgcatggag gcctgcatgc tcaatggcac tgtcattggg cccgggaaga ctgtgatgat   8040
cgatgtgtgc acgacctgcc gctgcatggt gcaggtgggg gtcatctctg gattcaagct   8100
ggagtgcagg aagaccacct gcaacccctg ccccctgggt tacaaggaag aaaataacac   8160
aggtgaatgt tgtgggagat gtttgcctac ggcttgcacc attcagctaa gaggaggaca   8220
gatcatgaca ctgaagcgtg atgagacgct ccaggatggc tgtgatactc acttctgcaa   8280
ggtcaatgag agaggagagt acttctggga gaagagggtc acaggctgcc caccctttga   8340
tgaacacaag tgtctggctg agggaggtaa aattatgaaa attccaggca cctgctgtga   8400
cacatgtgag gagcctgagt gcaacgacat cactgccagg ctgcagtatg tcaaggtggg   8460
aagctgtaag tctgaagtag aggtggatat ccactactgc cagggcaaat gtgccagcaa   8520
agccatgtac tccattgaca tcaacgatgt gcaggaccag tgctcctgct gctctccgac   8580
acggacggag cccatgcagg tggccctgca ctgcaccaat ggctctgttg tgtaccatga   8640
ggttctcaat gccatggagt gcaaatgctc ccccaggaag tgcagcaagt gaggctgctg   8700
cagctgcatg ggtgcctgct gctgcctgcc ttggcctgat ggccaggcca gagtgctgcc   8760
agtcctctgc atgttctgct cttgtgccct tctgagccca caataaaggc tgagctctta   8820
tcttgcaaaa ggc                                                      8833
```

```
<210> SEQ ID NO 3
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

gccagggacc uaagacacau gucccuggc                                   29


<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'-O-Methyl nucleotide
<220> FEATURE:
<221> NAME/KEY: modified_base
<222> LOCATION: (30)..(30)
<223> OTHER INFORMATION: Inverted nucleotide

<400> SEQUENCE: 4

gccagggacc uaagacacau gucccuggct                                  30


<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'-O-Methyl nucleotide
<220> FEATURE:
<221> NAME/KEY: modified_base
<222> LOCATION: (30)..(30)
<223> OTHER INFORMATION: Inverted nucleotide

<400> SEQUENCE: 5

gccagggacc uaagacacau gucccuggct                                  30


<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(29)
<223> OTHER INFORMATION: 2'-O-Methyl nucleotide
<220> FEATURE:
<221> NAME/KEY: modified_base
<222> LOCATION: (30)..(30)
```

<223> OTHER INFORMATION: Inverted nucleotide

<400> SEQUENCE: 6
gccagggacc uaagacacau gucccuggct 30

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (1)..(21)
<223> OTHER INFORMATION: 2'-O-Methyl nucleotide
<220> FEATURE:
<221> NAME/KEY: modified_base
<222> LOCATION: (22)..(22)
<223> OTHER INFORMATION: Inverted nucleotide

<400> SEQUENCE: 7
gggaccuaag acacaugucc ct 22

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<221> NAME/KEY: modified_base
<222> LOCATION: (1)..(4)
<223> OTHER INFORMATION: 2'-O-Methyl nucleotide
<220> FEATURE:
<221> NAME/KEY: modified_base
<222> LOCATION: (8)..(18)
<223> OTHER INFORMATION: 2'-O-Methyl nucleotide
<220> FEATURE:
<221> NAME/KEY: modified_base
<222> LOCATION: (20)..(20)
<223> OTHER INFORMATION: 2'-O-Methyl nucleotide
<220> FEATURE:
<221> NAME/KEY: misc_feature
<222> LOCATION: (20)..(21)
<223> OTHER INFORMATION: Phosphorothioate linkage
<220> FEATURE:
<221> NAME/KEY: modified_base
<222> LOCATION: (22)..(22)
<223> OTHER INFORMATION: 2'-O-Methyl nucleotide
<220> FEATURE:
<221> NAME/KEY: modified_base
<222> LOCATION: (27)..(28)
<223> OTHER INFORMATION: 2'-O-Methyl nucleotide
<220> FEATURE:
<221> NAME/KEY: modified_base
<222> LOCATION: (30)..(30)
<223> OTHER INFORMATION: 2'-O-Methyl nucleotide
<220> FEATURE:
<221> NAME/KEY: modified_base
<222> LOCATION: (33)..(34)
<223> OTHER INFORMATION: 2'-O-Methyl nucleotide
<220> FEATURE:
<221> NAME/KEY: modified_base
<222> LOCATION: (36)..(39)
<223> OTHER INFORMATION: 2'-O-Methyl nucleotide
<220> FEATURE:
<221> NAME/KEY: modified_base

```
<222> LOCATION: (40)..(40)
<223> OTHER INFORMATION: Inverted nucleotide

<400> SEQUENCE: 8

gcgugcagug ccuucggccg tgcggtgccu ccgucacgct                          40


<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9

acaugugucu uaggucccug gc                                             22


<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(22)
<223> OTHER INFORMATION: 2'-O-Methyl nucleotide
<220> FEATURE:
<221> NAME/KEY: modified_base
<222> LOCATION: (23)..(23)
<223> OTHER INFORMATION: Inverted nucleotide

<400> SEQUENCE: 10

acaugugucu uaggucccug gct                                            23
```